US006518405B1

(12) United States Patent
Dowling et al.

(10) Patent No.: US 6,518,405 B1
(45) Date of Patent: Feb. 11, 2003

(54) MAMMALIAN PROTEINASES; OXIDOREDUCTASES; RELATED REAGENTS

(75) Inventors: Lynette M. Dowling, Redwood City, CA (US); Constance F. Huffine, San Francisco, CA (US); Daniel M. Gorman, Newark, CA (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 09/546,553

(22) Filed: Apr. 10, 2000

Related U.S. Application Data

(62) Division of application No. 08/813,150, filed on Mar. 7, 1997, now Pat. No. 6,069,229.

(51) Int. Cl.$^7$ .................. C07K 16/00; G01N 33/53; A61K 39/395; A61K 39/40
(52) U.S. Cl. .................. 530/387.9; 530/388.1; 530/388.26; 530/389.1; 530/391.3; 435/975; 435/7.1; 424/146.1; 424/139.1; 424/130.1
(58) Field of Search .................. 530/387.9, 388.1, 530/387.3, 387.1, 388.26, 388.7, 388.73, 388.75, 389.1, 391.3, 391.5, 391.7, 350, 300, 827; 930/250; 424/130.1, 134.1, 139.1, 141.1, 146.1; 435/7.1, 70.2, 70.3, 451, 452, 189, 975

(56) References Cited

U.S. PATENT DOCUMENTS

| | | | |
|---|---|---|---|
| 5,518,911 A | | 5/1996 | Abo et al. .................. 435/194 |
| 5,660,978 A | * | 8/1997 | Kwan et al. .................. 435/5 |
| 6,069,229 A | * | 5/2000 | Dowling et al. ............ 530/300 |

FOREIGN PATENT DOCUMENTS

| | | |
|---|---|---|
| WO | WO 90/00195 | 1/1990 |
| WO | WO 97/07198 | 2/1997 |
| WO | WO 98/39421 | 9/1998 |

OTHER PUBLICATIONS

L.–C. Au, et al., *Genbank*, Accession No. L08780, M75916, Jun. 8, 1993. "Calloselasma rhodostoma rhodostomin and hemorrhagic protein mRNA, complete cds".
C. Auffrey, et al., *Genbank*, Accession No. Z42175, Sep. 21, 1995. "H. sapiens partial cDNA sequence; clone c–0be05".
A.W. Bach, et al., *Genbank*, Accession No. M68840, J03792, Jan. 7, 1995. "Humanmonoamine oxidase A (MAOA) mRNA, complete cds".
A.W. Bach, et al., *Genbank*, Accession No. M69177, J03793, Jan. 7, 1995. "Human monoamine oxidase B (MAOB) mRNA, complete cds".
R.A. Black, et al., *Genbank*, Accession No. U69611, Mar. 5, 1997. "Human TNF–alpha converting enzyme mRNA, complete cds".
J. Bukh, et al., *Genbank*, Accession No. U10234, Aug. 26, 1994. "Hepatitis C virus isolate US6 core protein gene".

Myriam C. Capone, et al., *Journal of Immunology*, 157:969–973, 1996. "Identification Through Bioinformatics of cDNAs Encoding Human Thymic Shared Ag–1/Stem Cell Ag–2".
P. Chardin, et al., *Genbank*, Accession No. X06820, Oct. 24, 1996. "H. sapiens rhoB gene mRNA".
P. Chardin, et al., *Genbank*, Accession No. X06821, Sep. 12, 1993. "Human rhoC mRNA (clone 9)".
Charles C. Chu and William E. Paul, *Proc. Natl. Acad. Sci. USA*, 94:2507–2512, Mar. 18, 1997. "Fig. 1, an interleukin 4–induced mouse B cell gene isolated by cDNA representational difference analysis".
Charles C. Chu and W.E. Paul, *GenBank*, Accession No. U70429, Apr. 4, 1997. Definition: Mus musculus interleukin–4 induced gene–1 (Fig 1) mRNA, complete cds.
Dagmar Diekmann, et al., *Meth. Enzymol.*, 256:207–215, 1995. "[9] In Vitro Binding Assay for Interactions of Rho and Rac with GTPase–Activating Proteins and Effectors".
K.P. Fagan, et al., *Genbank*, Accession No. L205081, Jan. 9, 1995. "Human GTPase (rhoC) mRNA, complete cds".
Robert J. Gould, et al., *Proc. Soc. Exp. Biol. Med.*, 195:168–171, 1990. "Distintegrins: A Family of Integrin Inhibitory Proteins from Viper Venoms (43129B)".
L. Hall, *Genbank*, Accession No. Y08617, Oct. 9, 1996. "M. fascicularis mRNA for tDMC III protein".
Alan Hall, *Molecular Biology of the Cell.*, 3:475–479, May 1992. "Ras–Related GTPases and the Cytoskeleton".
B. Herren, et al., *Genbank*, Accession No. U46005, Feb. 28, 1997. "Human MDC15 mRNA, complete cds".
Rolf Hilgenfield, *Current Opinion in Structural Biology*, 5:810–817, 1995. "Regulatory GTPases".
L. Hillier, et al., *Genbank*, Accession No. H07061, Jun. 21, 1995. "y181d09.r1 Homo sapiens cDNA clone 44782 5' ".
L. Hillier, et al., *Genbank*, Accession No. H13318, Jun. 27, 1995. "y172c03.r1 Homo sapiens cDNA clone 43468 5' ".
L. Hillier, et al., *Genbank*, Accession No. H96929, Dec. 11, 1995. "yu01c03.r1 Homo sapiens cDNA clone 232516 5' ".
L. Hillier, et al., *Genbank*, Accession No. N52992, Jan. 28, 1997. "yv30c08.s1 Soares fetal liver spleen 1NFLS Homo sapiens cDNA clone 244238 3' ".
L. Hillier, et al., *Genbank*, Accession No. R13953, Apr. 12, 1995. "yf68c02.r1 Homo sapiens cDNA clone 27599 5' ".
Lawrence A. Hite, et al., *Biochemistry*, 31:6203–6211, 1992. "Sequence of a cDNA Clone Encoding the Zinc Metalloproteinase Hemorrhagic Toxin e from *Crotalus atrox*: Evidence for Signal, Zymogen, and Disintegrin–like Structures".

(List continued on next page.)

Primary Examiner—S. Devi
(74) *Attorney, Agent, or Firm*—Tom Brody; Sheela Mohan-Peterson; Edwin P. Ching

(57) ABSTRACT

Nucleic acids encoding various proteases, from a mammal, reagents related thereto, including specific antibodies, and purified proteins are described. Methods of using said reagents and related diagnostic kits are also provided.

6 Claims, No Drawings

OTHER PUBLICATIONS

Neil A. Hotchln, et al., *Cancer Surveys*, 27:311–322, 1996. "Regulation of the Actin Cytoskeleton, Integrins and Cell Growth by the Rho Family of Small GTPases".

M. Ikeuchi, et al., *Genbank*, Accession No. M74841, Aug. 13, 1991. "Synechocystis sp. PCC 6803 small photosystem II component (psbK) gene, complete cds".

D. Jaehner, et al., *Genbank*, Accession No. M74295, Aug. 5, 1991. "Rat rhoB gene mRNA, complete cds".

Kouji Kuno, et al., *J. Biol. Chem.*, 272(1):556–562, Jan. 3, 1997. "Molecular Cloning of a New Type of Metalloproteinase–disintegrin Family Protein with Thrombospondin Motifs as an Inflammation Associated Gene".

Lewin, Benjamin (ed), *Genes* ($2^{nd}$ edition) Wiley & Sons 1983, p. 457.

P. Madaule, et al., *Genbank*, Accession No. M12174, Aug. 4, 1996. "Human ras–related rho mRNA (clone 6), partial cds".

Chris G.F. Mueller, et al., *J. Exp. Med.*, 186(5):655–663, Aug. 29, 1997. "Polymerase Chain Reaction Selects a Novel Disintegrin Proteinase from CD40–Activated Germinal Center Dendritic Cells".

Christopher C. Moser, et al., *J. Bioenergetics and Biomembranes*, 27(3):263–274, 1995. "Biological Electron Transfer".

Catherine Nobes, et al., *Current Opinion in Genetics and Development*, 4:77–81, 1994. "Regulation and function of the Rho subfamily of small GTPases".

Claude Nuoffer, et al., *Annu. Rev. Biochem.*, 63:949–990, 1994. "GTPases:Multifunctional Molecular Switches Regulating Vesicular Traffic".

M.J.I. Paine, *Genbank*, Accession No. X68251, S49385, Jul. 21, 1995. "B. jararaca mRNA for jararhagin".

F. Segade, et al., *Genbank*, Accession No. X80638, X80898, Apr. 24, 1996. "M. Musculus rhoC mRNA".

Marcel Spaargaren, et al., *Gene Expression*, 4:345–356, 1995. "Signal Transduction by Ras–Like GTPases: A Potential Target for Anticancer Drugs".

C. Steward, *Genbank*, Accession No. Z92544, Oct. 9, 1997. Definition: Human DNA sequence from cosmid 313D11 from a contig on the short arm of chromosome 16. Contains ESTs, STS and CpG islands.

Marc Symons, *Trends in Bioch. Sci. (TIBS)*, 21:178–181, May 1996. "Rho family GTPases: the cytoskeleton and beyond".

F.W.L. Tsui, et al., *Genbank*, Accession No. M92418, Jun. 1, 1993. "Mouse cysteine proteinase inhibitor (MS2) mRNA sequence".

Bert L. Vallee, et al., *Biochemistry*, 29:5647–5659, 1990. "Zinc Coordination, Fuction, and Structure of Zinc Enzymes and Other Proteins".

Bert L. Vallee, et al., *PNAS*, 87:220–224, 1990. "Active–site zinc ligands and activated $H_2O$ of zinc enzymes".

Harold E. Van Wart, et al., *PNAS*, 87:5578–5582, 1990. The cysteine switch: A principle of regulation of metalloproteinase activity with potential applicability to the entire matrix metalloproteinase gene family.

G. Weskamp, et al., *Genbank*, Accession No. U41766, Mar. 22, 1996. "Human metalloproteinase/disintegrin/cysteine–rich protein precursor (MDC9) mRNA, complete cds".

T. Yagami–Hiromasa, et al., *Genbank*, Accession No. D50411, Nov. 7, 1995. "Mouse mRNA for meltrin alpha".

\* cited by examiner

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2280 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 61..1470

(xi) SEQUENCE DESCRIPTION: SEQ ID NO:1:

```
CGCCCGGGCA GGTGAGAAAT TGGAGAAGAT AAAACTGGAC ACTGGGGAGA CCACAACTTC         60

ATG CTG CGT GGG ATC TCC CAG CTA CCT GCA GTG GCC ACC ATG TCT TGG         108
Met Leu Arg Gly Ile Ser Gln Leu Pro Ala Val Ala Thr Met Ser Trp
  1               5                  10                  15

GTC CTG CTG CCT GTA CTT TGG CTC ATT GTT CAA ACT CAA GCA ATA GCC         156
Val Leu Leu Pro Val Leu Trp Leu Ile Val Gln Thr Gln Ala Ile Ala
             20                  25                  30

ATA AAG CAA ACA CCT GAA TTA ACG CTC CAT GAA ATA GTT TGT CCT AAA         204
Ile Lys Gln Thr Pro Glu Leu Thr Leu His Glu Ile Val Cys Pro Lys
         35                  40                  45

AAA CTT CAC ATT TTA CAC AAA AGA GAG ATC AAG AAC AAC CAG ACA GAA         252
Lys Leu His Ile Leu His Lys Arg Glu Ile Lys Asn Asn Gln Thr Glu
     50                  55                  60

AAG CAT GGC AAA GAG GAA AGG TAT GAA CCT GAA GTT CAA TAT CAG ATG         300
Lys His Gly Lys Glu Glu Arg Tyr Glu Pro Glu Val Gln Tyr Gln Met
 65                  70                  75                  80

ATC TTA AAT GGA GAA GAA ATC ATT CTC TCC CTA CAA AAA ACC AAG CAC         348
Ile Leu Asn Gly Glu Glu Ile Ile Leu Ser Leu Gln Lys Thr Lys His
                 85                  90                  95

CTC CTG GGG CCA GAC TAC ACT GAA ACA TTG TAC TCA CCC AGA GGA GAG         396
Leu Leu Gly Pro Asp Tyr Thr Glu Thr Leu Tyr Ser Pro Arg Gly Glu
            100                 105                 110

GAA ATT ACC ACG AAA CCT GAG AAC ATG GAA CAC TGT TAC TAT AAA GGA         444
Glu Ile Thr Thr Lys Pro Glu Asn Met Glu His Cys Tyr Tyr Lys Gly
        115                 120                 125

AAC ATC CTA AAT GAA AAG AAT TCT GTT GCC AGC ATC AGT ACT TGT GAC         492
Asn Ile Leu Asn Glu Lys Asn Ser Val Ala Ser Ile Ser Thr Cys Asp
    130                 135                 140

GGG TTG AGA GGA TAC TTC ACA CAT CAT CAC CAA AGA TAC CAG ATA AAA         540
Gly Leu Arg Gly Tyr Phe Thr His His His Gln Arg Tyr Gln Ile Lys
145                 150                 155                 160

CCT CTG AAA AGC ACA GAC GAG AAA GAA CAT GCC GTC TTT ACA TCT AAC         588
Pro Leu Lys Ser Thr Asp Glu Lys Glu His Ala Val Phe Thr Ser Asn
                165                 170                 175

CAG GAG GAA CAA GAC CCA GCT AAC CAC ACA TGT GGT GTG AAG AGC ACT         636
Gln Glu Glu Gln Asp Pro Ala Asn His Thr Cys Gly Val Lys Ser Thr
            180                 185                 190

GAC GGG AAA CAA GGC CCA ATT CGA ATC TCT AGA TCA CTC AAA GCC CCA         684
Asp Gly Lys Gln Gly Pro Ile Arg Ile Ser Arg Ser Leu Lys Ser Pro
        195                 200                 205

GAG AAA GAA GAC TTT CTT CGG GCA CAG AAA TAC ATT GAT CTC TAT TTG         732
```

-continued

```
Glu Lys Glu Asp Phe Leu Arg Ala Gln Lys Tyr Ile Asp Leu Tyr Leu
    210                 215                 220

GTG CTG GAT AAT GCC TTT TAT AAG AAC TAT AAT GAG AAT CTA ACT CTG        780
Val Leu Asp Asn Ala Phe Tyr Lys Asn Tyr Asn Glu Asn Leu Thr Leu
225                 230                 235                 240

ATA AGA AGC TTT GTG TTT GAT GTG ATG AAC CTA CTC AAT GTG ATA TAT        828
Ile Arg Ser Phe Val Phe Asp Val Met Asn Leu Leu Asn Val Ile Tyr
                245                 250                 255

AAC ACC ATA GAT GTT CAA GTG GCC TTG GTA GGT ATG GAA ATC TGG TCT        876
Asn Thr Ile Asp Val Gln Val Ala Leu Val Gly Met Glu Ile Trp Ser
            260                 265                 270

GAT GGG GAT AAG ATA AAG GTG GTG CCC AGC GCA AGC ACC ACG TTT GAC        924
Asp Gly Asp Lys Ile Lys Val Val Pro Ser Ala Ser Thr Thr Phe Asp
        275                 280                 285

AAC TTC CTG AGA TGG CAC AGT TCT AAC CCG GGG AAA AAG ATC CAC GAC        972
Asn Phe Leu Arg Trp His Ser Ser Asn Pro Gly Lys Lys Ile His Asp
    290                 295                 300

CAT GCT CAG CTT CTC AGC GGG ATT AGC TTC AAC AAT CGA CGT GTG GGA       1020
His Ala Gln Leu Leu Ser Gly Ile Ser Phe Asn Asn Arg Arg Val Gly
305                 310                 315                 320

CTG GCA GCT TCA AAT TCC TTG TGT TCC CCA TCT TCG GTT GCT GTT ATT       1068
Leu Ala Ala Ser Asn Ser Leu Cys Ser Pro Ser Ser Val Ala Val Ile
                325                 330                 335

GAG GCT AAA AAA AAG AAT AAT GTG GCT CTT GTA GGA GTG ATG TCA CAT       1116
Glu Ala Lys Lys Lys Asn Asn Val Ala Leu Val Gly Val Met Ser His
            340                 345                 350

GAG CTG GGC CAT GTC CTT GGT ATG CCT GAT GTT CCA TTC AAC ACC AAG       1164
Glu Leu Gly His Val Leu Gly Met Pro Asp Val Pro Phe Asn Thr Lys
        355                 360                 365

TGT CCC TCT GGC AGT TGT GTG ATG AAT CAG TAT CTG AGT TCA AAA TTC       1212
Cys Pro Ser Gly Ser Cys Val Met Asn Gln Tyr Leu Ser Ser Lys Phe
    370                 375                 380

CCA AAG GAT TTC AGT ACA TCT TGC CGT GCA CAT TTT GAA AGA TAC CTT       1260
Pro Lys Asp Phe Ser Thr Ser Cys Arg Ala His Phe Glu Arg Tyr Leu
385                 390                 395                 400

TTA TCT CAG AAA CCA AAG TGC CTG CTG CAA GCA CCT ATT CCT ACA AAT       1308
Leu Ser Gln Lys Pro Lys Cys Leu Leu Gln Ala Pro Ile Pro Thr Asn
                405                 410                 415

ATA ATG ACA ACA CCA GTG TGT GGG AAC CAC CTT CTA GAA GTG GGA GAA       1356
Ile Met Thr Thr Pro Val Cys Gly Asn His Leu Leu Glu Val Gly Glu
            420                 425                 430

GAC TGT GAT TGT GGC TCT CCT AAG GAG TGT ACC AGT CTC TGC TGT GAA       1404
Asp Cys Asp Cys Gly Ser Pro Lys Glu Cys Thr Ser Leu Cys Cys Glu
        435                 440                 445

GCC CTA ACG TGT AAA CTG AAG CCT GGA ACT GAT TGC GGA GGA GAT GCT       1452
Ala Leu Thr Cys Lys Leu Lys Pro Gly Thr Asp Cys Gly Gly Asp Ala
    450                 455                 460

CCA AAC CAT ACC ACA GAG TGAATCCAAA GTCTGCTTCA CTGAGATGCT              1500
Pro Asn His Thr Thr Glu
465                 470

ACCTTGCCAG GACAAGAACC AAGAACTCTA ACTGTCCCAG GAATCTTGTG AATTTTCACC     1560

CATAATGGTC TTTCACTTGT CATTCTACTT TCTATATTGT TATCAGTCCA GGAAACAGGT     1620

AAACAGATGT AATTAGAGAC ATTGGCTCTT TGTTTAGGCC TAATCTTTCT TTTTACTTTT     1680

TTTTTTCTTT TTTCTTTTTT TTTAAAGATC ATGAATTTGT GACTTAGTTC TGCCCTTTGG     1740

AGAACAAAAG AAAGCAGTCT TCCATCAAAT CACCTTAAAA TGCACGGCTA AACTATTCAG     1800

AGTTAACACT CCAGAATTGT TAAATTACAA GTACTATGCT TTAATGCTTC TTTCATCTTA     1860
```

-continued

```
CTAGTATGGC CTATAAAAAA AATAATACCA CTTGATGGGT GAAGGCTTTG GCAATAGAAA      1920

GAAGAATAGA ATTCAGGTTT TATGTTATTC CTCTGTGTTC ACTTCGCCTT GCTCTTGAAA      1980

GTGCAGTATT TTTCTACATC ATGTCGAGAA TGATTCAATG TAAATATTTT TCATTTTATC      2040

ATGTATATCC TATACACACA TCTCCTTCAT CATCATATAT GAAGTTTATT TTGAGAAGTC      2100

TACATTGCTT ACATTTTAAT TGAGCCAGCA AAGAAGGCTT AATGATTTAT TGAACCATAA      2160

TGTCAATAAA AACACAACTT TTGAGGCAAA AAAAAAAAAA AAAAAAAAAA AAAAAAAAAA      2220

AAAAAAAAAA AAAAAAAAAA AAGAAAAAAA AAAAAAAAAA AAAAAGACCT TGCCCGGGCG      2280
```

(2) INFORMATION FOR SEQ ID NO:2:

(i) SEQUENCE CHARACTERISTICS:
        (A) LENGTH: 470 amino acids
        (B) TYPE: amino acid
        (D) TOPOLOGY: linear (ii) MOLECULE TYPE: protein (xi) SEQUENCE DESCRIPTION: SEQ ID NO:2:

```
Met Leu Arg Gly Ile Ser Gln Leu Pro Ala Val Ala Thr Met Ser Trp
 1               5                  10                  15

Val Leu Leu Pro Val Leu Trp Leu Ile Val Gln Thr Gln Ala Ile Ala
                20                  25                  30

Ile Lys Gln Thr Pro Glu Leu Thr Leu His Glu Ile Val Cys Pro Lys
            35                  40                  45

Lys Leu His Ile Leu His Lys Arg Glu Ile Lys Asn Asn Gln Thr Glu
        50                  55                  60

Lys His Gly Lys Glu Glu Arg Tyr Glu Pro Val Gln Tyr Gln Met
65                  70                  75                  80

Ile Leu Asn Gly Glu Glu Ile Ile Leu Ser Leu Gln Lys Thr Lys His
                85                  90                  95

Leu Leu Gly Pro Asp Tyr Thr Glu Thr Leu Tyr Ser Pro Arg Gly Glu
               100                 105                 110

Glu Ile Thr Thr Lys Pro Glu Asn Met Glu His Cys Tyr Tyr Lys Gly
           115                 120                 125

Asn Ile Leu Asn Glu Lys Asn Ser Val Ala Ser Ile Ser Thr Cys Asp
       130                 135                 140

Gly Leu Arg Gly Tyr Phe Thr His His Gln Arg Tyr Gln Ile Lys
145                 150                 155                 160

Pro Leu Lys Ser Thr Asp Glu Lys Glu His Ala Val Phe Thr Ser Asn
                165                 170                 175

Gln Glu Glu Gln Asp Pro Ala Asn His Thr Cys Gly Val Lys Ser Thr
            180                 185                 190

Asp Gly Lys Gln Gly Pro Ile Arg Ile Ser Arg Ser Leu Lys Ser Pro
        195                 200                 205

Glu Lys Glu Asp Phe Leu Arg Ala Gln Lys Tyr Ile Asp Leu Tyr Leu
    210                 215                 220

Val Leu Asp Asn Ala Phe Tyr Lys Asn Tyr Glu Asn Leu Thr Leu
225                 230                 235                 240

Ile Arg Ser Phe Val Phe Asp Val Met Asn Leu Leu Asn Val Ile Tyr
                245                 250                 255

Asn Thr Ile Asp Val Gln Val Ala Leu Val Gly Met Glu Ile Trp Ser
            260                 265                 270

Asp Gly Asp Lys Ile Lys Val Val Pro Ser Ala Ser Thr Thr Phe Asp
        275                 280                 285
```

```
Asn Phe Leu Arg Trp His Ser Ser Asn Pro Gly Lys Lys Ile His Asp
    290                 295                 300

His Ala Gln Leu Leu Ser Gly Ile Ser Phe Asn Asn Arg Arg Val Gly
305                 310                 315                 320

Leu Ala Ala Ser Asn Ser Leu Cys Ser Pro Ser Ser Val Ala Val Ile
                325                 330                 335

Glu Ala Lys Lys Lys Asn Asn Val Ala Leu Val Gly Val Met Ser His
                340                 345                 350

Glu Leu Gly His Val Leu Gly Met Pro Asp Val Pro Phe Asn Thr Lys
            355                 360                 365

Cys Pro Ser Gly Ser Cys Val Met Asn Gln Tyr Leu Ser Ser Lys Phe
    370                 375                 380

Pro Lys Asp Phe Ser Thr Ser Cys Arg Ala His Phe Glu Arg Tyr Leu
385                 390                 395                 400

Leu Ser Gln Lys Pro Lys Cys Leu Leu Gln Ala Pro Ile Pro Thr Asn
                405                 410                 415

Ile Met Thr Thr Pro Val Cys Gly Asn His Leu Leu Glu Val Gly Glu
            420                 425                 430

Asp Cys Asp Cys Gly Ser Pro Lys Glu Cys Thr Ser Leu Cys Cys Glu
            435                 440                 445

Ala Leu Thr Cys Lys Leu Lys Pro Gly Thr Asp Cys Gly Gly Asp Ala
    450                 455                 460

Pro Asn His Thr Thr Glu
465                 470

(2) INFORMATION FOR SEQ ID NO:3:

(i) SEQUENCE CHARACTERISTICS:
        (A) LENGTH: 1780 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 66..1766

(xi) SEQUENCE DESCRIPTION: SEQ ID NO:3:

AGTGGAGAGG ACCGCGCTGT CCTGCTGTCA CCAAGAGCTG GAGACACCAT CTCCCACCGA     60

GAGTC ATG GCC CCA TTG GCC CTG CAC CTC CTC GTC CTC GTC CCC ATC        107
      Met Ala Pro Leu Ala Leu His Leu Leu Val Leu Val Pro Ile
        1               5                  10

CTC CTC AGC CTG GTG GCC TCC CAG GAC TGG AAG GCT GAA CGC AGC CAA      155
Leu Leu Ser Leu Val Ala Ser Gln Asp Trp Lys Ala Glu Arg Ser Gln
 15                  20                  25                  30

GAC CCC TTC GAG AAA TGC ATG CAG GAT CCT GAC TAT GAG CAG CTG CTC      203
Asp Pro Phe Glu Lys Cys Met Gln Asp Pro Asp Tyr Glu Gln Leu Leu
                 35                  40                  45

AAG GTG GTG ACC TGG GGG CTC AAT CGG ACC CTG AAG CCC CAG AGG GTG      251
Lys Val Val Thr Trp Gly Leu Asn Arg Thr Leu Lys Pro Gln Arg Val
             50                  55                  60

ATT GTG GTT GGC GCT GGT GTG GCC GGG CTG GTG GCC GCC AAG GTG CTC      299
Ile Val Val Gly Ala Gly Val Ala Gly Leu Val Ala Ala Lys Val Leu
         65                  70                  75

AGC GAT GCT GGA CAC AAG GTC ACC ATC CTG GAG GCA GAT AAC AGG ATC      347
Ser Asp Ala Gly His Lys Val Thr Ile Leu Glu Ala Asp Asn Arg Ile
 80                  85                  90
```

| | | | | | | | | | | | | | | | |
|---|---|---|---|---|---|---|---|---|---|---|---|---|---|---|---|
| GGG | GGC | CGC | ATC | TTC | ACC | TAC | CGG | GAC | CAG | AAC | ACG | GGC | TGG | ATT | GGG | 395 |
| Gly | Gly | Arg | Ile | Phe | Thr | Tyr | Arg | Asp | Gln | Asn | Thr | Gly | Trp | Ile | Gly |
| 95 | | | | 100 | | | | | 105 | | | | | 110 | |

```
GGG GGC CGC ATC TTC ACC TAC CGG GAC CAG AAC ACG GGC TGG ATT GGG      395
Gly Gly Arg Ile Phe Thr Tyr Arg Asp Gln Asn Thr Gly Trp Ile Gly
 95              100                 105                 110

GAG CTG GGA GCC ATG CGC ATG CCC AGC TCT CAC AGG ATC CTC CAC AAG      443
Glu Leu Gly Ala Met Arg Met Pro Ser Ser His Arg Ile Leu His Lys
                115                 120                 125

CTC TGC CAG GGC CTG GGG CTC AAC CTG ACC AAG TTC ACC CAG TAC GAC      491
Leu Cys Gln Gly Leu Gly Leu Asn Leu Thr Lys Phe Thr Gln Tyr Asp
                130                 135                 140

AAG AAC ACG TGG ACG GAG GTG CAC GAA GTG AAG CTG CGC AAC TAT GTG      539
Lys Asn Thr Trp Thr Glu Val His Glu Val Lys Leu Arg Asn Tyr Val
            145                 150                 155

GTG GAG AAG GTG CCC GAG AAG CTG GGC TAC GCC TTG CGT CCC CAG GAA      587
Val Glu Lys Val Pro Glu Lys Leu Gly Tyr Ala Leu Arg Pro Gln Glu
160                 165                 170

AAG GGC CAC TCG CCC GAA GAC ATC TAC CAG ATG GCT CTC AAC CAG GCC      635
Lys Gly His Ser Pro Glu Asp Ile Tyr Gln Met Ala Leu Asn Gln Ala
175                 180                 185                 190

CTC AAA GAC CTC AAG GCA CTG GGC TGC AGA AAG GCG ATG AAG AAG TTT      683
Leu Lys Asp Leu Lys Ala Leu Gly Cys Arg Lys Ala Met Lys Lys Phe
                195                 200                 205

GAA AGG CAC ACG CTC TTG GAA TAT CTT CTC GGG GAG GGG AAC CTG AGC      731
Glu Arg His Thr Leu Leu Glu Tyr Leu Leu Gly Glu Gly Asn Leu Ser
                210                 215                 220

CGG CCG GCC GTG CAG CTT CTG GGA GAC GTG ATG TCC GAG GAT GGC TTC      779
Arg Pro Ala Val Gln Leu Leu Gly Asp Val Met Ser Glu Asp Gly Phe
                225                 230                 235

TTC TAT CTC AGC TTC GCC GAG GCC CTC CGG GCC CAC AGC TGC CTC AGC      827
Phe Tyr Leu Ser Phe Ala Glu Ala Leu Arg Ala His Ser Cys Leu Ser
240                 245                 250

GAC AGA CTC CAG TAC AGC CGC ATC GTG GGT GGC TGG GAC CTG CTG CCG      875
Asp Arg Leu Gln Tyr Ser Arg Ile Val Gly Gly Trp Asp Leu Leu Pro
255                 260                 265                 270

CGC GCG CTG CTG AGC TCG CTG TCC GGG CTT GTG CTG TTG AAC GCG CCC      923
Arg Ala Leu Leu Ser Ser Leu Ser Gly Leu Val Leu Leu Asn Ala Pro
                275                 280                 285

GTG GTG GCG ATG ACC CAG GGA CCG CAC GAT GTG CAC GTG CAG ATC GAG      971
Val Val Ala Met Thr Gln Gly Pro His Asp Val His Val Gln Ile Glu
                290                 295                 300

ACC TCT CCC CCG GCG CGG AAT CTG AAG GTG CTG AAG GCC GAC GTG GTG     1019
Thr Ser Pro Pro Ala Arg Asn Leu Lys Val Leu Lys Ala Asp Val Val
            305                 310                 315

CTG CTG ACG GCG AGC GGA CCG GCG GTG AAG CGC ATC ACC TTC TCG CCG     1067
Leu Leu Thr Ala Ser Gly Pro Ala Val Lys Arg Ile Thr Phe Ser Pro
            320                 325                 330

CCG CTG CCC CGC CAC ATG CAG GAG GCG CTG CGG AGG CTG CAC TAC GTG     1115
Pro Leu Pro Arg His Met Gln Glu Ala Leu Arg Arg Leu His Tyr Val
335                 340                 345                 350

CCG GCC ACC AAG GTG TTC CTA AGC TTC CGC AGG CCC TTC TGG CGC GAG     1163
Pro Ala Thr Lys Val Phe Leu Ser Phe Arg Arg Pro Phe Trp Arg Glu
                355                 360                 365

GAG CAC ATT GAA GGC GGC CAC TCA AAC ACC GAT CGC CCG TCG CGC ATG     1211
Glu His Ile Glu Gly Gly His Ser Asn Thr Asp Arg Pro Ser Arg Met
                370                 375                 380

ATT TTC TAC CCG CCG CCG CGC GAG GGC GCG CTG CTG CTG GCC TCG TAC     1259
Ile Phe Tyr Pro Pro Pro Arg Glu Gly Ala Leu Leu Leu Ala Ser Tyr
                385                 390                 395

ACG TGG TCG GAC GCG GCG GCA GCG TTC GCC GGC TTG AGC CGG GAA GAG     1307
Thr Trp Ser Asp Ala Ala Ala Ala Phe Ala Gly Leu Ser Arg Glu Glu
```

```
                400                 405                 410
GCG TTG CGC TTG GCG CTC GAC GAC GTG GCG GCA TTG CAC GGG CCT GTC        1355
Ala Leu Arg Leu Ala Leu Asp Asp Val Ala Ala Leu His Gly Pro Val
415                 420                 425                 430

GTG CGC CAG CTC TGG GAC GGC ACC GGC GTC GTC AAG CGT TGG GCG GAG        1403
Val Arg Gln Leu Trp Asp Gly Thr Gly Val Val Lys Arg Trp Ala Glu
                435                 440                 445

GAC CAG CAC AGC CAG GGT GGC TTT GTG GTA CAG CCG CCG GCG CTC TGG        1451
Asp Gln His Ser Gln Gly Gly Phe Val Val Gln Pro Pro Ala Leu Trp
            450                 455                 460

CAA ACC GAA AAG GAT GAC TGG ACG GTC CCT TAT GGC CGC ATC TAC TTT        1499
Gln Thr Glu Lys Asp Asp Trp Thr Val Pro Tyr Gly Arg Ile Tyr Phe
                465                 470                 475

GCC GGC GAG CAC ACC GCC TAC CCG CAC GGC TGG GTG GAG ACG GCG GTC        1547
Ala Gly Glu His Thr Ala Tyr Pro His Gly Trp Val Glu Thr Ala Val
            480                 485                 490

AAG TCG GCG CTG CGC GCC GCC ATC AAG ATC AAC AGC CGG AAG GGG CCT        1595
Lys Ser Ala Leu Arg Ala Ala Ile Lys Ile Asn Ser Arg Lys Gly Pro
495                 500                 505                 510

GCA TCG GAC ACG GCC AGC CCC GAG GGG CAC GCA TCT GAC ATG GAG GGG        1643
Ala Ser Asp Thr Ala Ser Pro Glu Gly His Ala Ser Asp Met Glu Gly
                515                 520                 525

CAG GGG CAT GTG CAT GGG GTG GCC AGC AGC CCC TCG CAT GAC CTG GCA        1691
Gln Gly His Val His Gly Val Ala Ser Ser Pro Ser His Asp Leu Ala
            530                 535                 540

AAG GAA GAA GGC AGC CAC CCT CCA GTC CAA GGC CAG TTA TCT CTC CAA        1739
Lys Glu Glu Gly Ser His Pro Pro Val Gln Gly Gln Leu Ser Leu Gln
                545                 550                 555

AAC ACG ACC CAC ACG AGG ACC TCG CAT TAAAGTATTT TCGG                    1780
Asn Thr Thr His Thr Arg Thr Ser His
            560                 565

(2) INFORMATION FOR SEQ ID NO:4:

(i) SEQUENCE CHARACTERISTICS:
        (A) LENGTH: 567 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Pro Leu Ala Leu His Leu Leu Val Leu Val Pro Ile Leu Leu
  1               5                  10                  15

Ser Leu Val Ala Ser Gln Asp Trp Lys Ala Glu Arg Ser Gln Asp Pro
                 20                  25                  30

Phe Glu Lys Cys Met Gln Asp Pro Asp Tyr Glu Gln Leu Leu Lys Val
             35                  40                  45

Val Thr Trp Gly Leu Asn Arg Thr Leu Lys Pro Gln Arg Val Ile Val
         50                  55                  60

Val Gly Ala Gly Val Ala Gly Leu Val Ala Ala Lys Val Leu Ser Asp
 65                  70                  75                  80

Ala Gly His Lys Val Thr Ile Leu Glu Ala Asp Asn Arg Ile Gly Gly
                 85                  90                  95

Arg Ile Phe Thr Tyr Arg Asp Gln Asn Thr Gly Trp Ile Gly Glu Leu
            100                 105                 110

Gly Ala Met Arg Met Pro Ser Ser His Arg Ile Leu His Lys Leu Cys
        115                 120                 125

Gln Gly Leu Gly Leu Asn Leu Thr Lys Phe Thr Gln Tyr Asp Lys Asn
```

-continued

```
            130                 135                 140
Thr Trp Thr Glu Val His Glu Val Lys Leu Arg Asn Tyr Val Val Glu
145                 150                 155                 160

Lys Val Pro Glu Lys Leu Gly Tyr Ala Leu Arg Pro Gln Glu Lys Gly
                165                 170                 175

His Ser Pro Glu Asp Ile Tyr Gln Met Ala Leu Asn Gln Ala Leu Lys
                180                 185                 190

Asp Leu Lys Ala Leu Gly Cys Arg Lys Ala Met Lys Lys Phe Glu Arg
                195                 200                 205

His Thr Leu Leu Glu Tyr Leu Leu Gly Glu Gly Asn Leu Ser Arg Pro
                210                 215                 220

Ala Val Gln Leu Leu Gly Asp Val Met Ser Glu Asp Gly Phe Phe Tyr
225                 230                 235                 240

Leu Ser Phe Ala Glu Ala Leu Arg Ala His Ser Cys Leu Ser Asp Arg
                245                 250                 255

Leu Gln Tyr Ser Arg Ile Val Gly Gly Trp Asp Leu Leu Pro Arg Ala
                260                 265                 270

Leu Leu Ser Ser Leu Ser Gly Leu Val Leu Leu Asn Ala Pro Val Val
                275                 280                 285

Ala Met Thr Gln Gly Pro His Asp Val His Val Gln Ile Glu Thr Ser
290                 295                 300

Pro Pro Ala Arg Asn Leu Lys Val Leu Lys Ala Asp Val Val Leu Leu
305                 310                 315                 320

Thr Ala Ser Gly Pro Ala Val Lys Arg Ile Thr Phe Ser Pro Pro Leu
                325                 330                 335

Pro Arg His Met Gln Glu Ala Leu Arg Arg Leu His Tyr Val Pro Ala
                340                 345                 350

Thr Lys Val Phe Leu Ser Phe Arg Arg Pro Phe Trp Arg Glu Glu His
                355                 360                 365

Ile Glu Gly Gly His Ser Asn Thr Asp Arg Pro Ser Arg Met Ile Phe
                370                 375                 380

Tyr Pro Pro Arg Glu Gly Ala Leu Leu Ala Ser Tyr Thr Trp
385                 390                 395                 400

Ser Asp Ala Ala Ala Phe Ala Gly Leu Ser Arg Glu Glu Ala Leu
                405                 410                 415

Arg Leu Ala Leu Asp Asp Val Ala Ala Leu His Gly Pro Val Val Arg
                420                 425                 430

Gln Leu Trp Asp Gly Thr Gly Val Val Lys Arg Trp Ala Glu Asp Gln
                435                 440                 445

His Ser Gln Gly Gly Phe Val Val Gln Pro Pro Ala Leu Trp Gln Thr
                450                 455                 460

Glu Lys Asp Asp Trp Thr Val Pro Tyr Gly Arg Ile Tyr Phe Ala Gly
465                 470                 475                 480

Glu His Thr Ala Tyr Pro His Gly Trp Val Glu Thr Ala Val Lys Ser
                485                 490                 495

Ala Leu Arg Ala Ala Ile Lys Ile Asn Ser Arg Lys Gly Pro Ala Ser
                500                 505                 510

Asp Thr Ala Ser Pro Glu Gly His Ala Ser Asp Met Glu Gly Gln Gly
                515                 520                 525

His Val His Gly Val Ala Ser Ser Pro Ser His Asp Leu Ala Lys Glu
                530                 535                 540

Glu Gly Ser His Pro Pro Val Gln Gly Gln Leu Ser Leu Gln Asn Thr
545                 550                 555                 560
```

```
       Thr His Thr Arg Thr Ser His
                   565

(2) INFORMATION FOR SEQ ID NO:5:

(i) SEQUENCE CHARACTERISTICS:
        (A) LENGTH: 2456 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 69..1925

(xi) SEQUENCE DESCRIPTION: SEQ ID NO:5:

GGGTCGACCA CGCGTCCGAC CAGGTCGGGG CCGGGTTCCG GTCGGGGAG CGGCTCCGGG          60

CGGCAGCT ATG AGG CGG GAC GTG CGC ATC CTG TTA CTG GGC GAG GCC CAG        110
         Met Arg Arg Asp Val Arg Ile Leu Leu Leu Gly Glu Ala Gln
           1               5                  10

GTG GGG AAG ACG TCG CTG ATC CTG TCC CTG GTG GGC GAG GAG TTC CCC         158
Val Gly Lys Thr Ser Leu Ile Leu Ser Leu Val Gly Glu Glu Phe Pro
 15              20                  25                  30

GAG GAG GTC CCT CCC CGC GCG GAG GAG ATC ACG ATC CCC GCG GAC GTC         206
Glu Glu Val Pro Pro Arg Ala Glu Glu Ile Thr Ile Pro Ala Asp Val
                 35                  40                  45

ACC CCG GAG AAG GTG CCC ACC CAC ATC GTG GAC TAC TCA GAA GCC GAG         254
Thr Pro Glu Lys Val Pro Thr His Ile Val Asp Tyr Ser Glu Ala Glu
             50                  55                  60

CAG ACG GAC GAG GAG CTG CGG GAG GAG ATC CAC AAG GCA AAC GTG GTG         302
Gln Thr Asp Glu Glu Leu Arg Glu Glu Ile His Lys Ala Asn Val Val
         65                  70                  75

TGT GTG GTG TAT GAC GTC TCT GAG GAG GCC ACC ATT GAG AAG ATT CGA         350
Cys Val Val Tyr Asp Val Ser Glu Glu Ala Thr Ile Glu Lys Ile Arg
     80                  85                  90

ACT AAG TGG ATC CCA CTG GTG AAT GGG GGG ACC ACG CAG GGG CCC AGG         398
Thr Lys Trp Ile Pro Leu Val Asn Gly Gly Thr Thr Gln Gly Pro Arg
 95                 100                 105                 110

GTG CCC ATC ATC CTA GTG GGC AAC AAG TCA GAC CTG CGG TCG GGG AGC         446
Val Pro Ile Ile Leu Val Gly Asn Lys Ser Asp Leu Arg Ser Gly Ser
                115                 120                 125

TCC ATG GAG GCC GTG CTC CCC ATC ATG AGC CAG TTT CCC GAG ATT GAG         494
Ser Met Glu Ala Val Leu Pro Ile Met Ser Gln Phe Pro Glu Ile Glu
            130                 135                 140

ACC TGC GTG GAG TGT TCG GCC AAG AAC CTG AGG AAC ATC TCA GAG CTG         542
Thr Cys Val Glu Cys Ser Ala Lys Asn Leu Arg Asn Ile Ser Glu Leu
        145                 150                 155

TTC TAC TAC GCC CAG AAG GCC GTC CTG CAT CCC ACA GCC CCC CTC TAT         590
Phe Tyr Tyr Ala Gln Lys Ala Val Leu His Pro Thr Ala Pro Leu Tyr
    160                 165                 170

GAC CCT GAG GCC AAG CAG TTG AGG CCC GCG TGC GCC CAG GCG CTG ACG         638
Asp Pro Glu Ala Lys Gln Leu Arg Pro Ala Cys Ala Gln Ala Leu Thr
175                 180                 185                 190

CGC ATC TTC AGG CTC TCA GAT CAG GAC CTG GAC CAG GCG CTC AGT GAC         686
Arg Ile Phe Arg Leu Ser Asp Gln Asp Leu Asp Gln Ala Leu Ser Asp
                195                 200                 205

GAA GAG CTC AAC GCT TTC CAG CAG AAA TCC TGC TTT GGG CAC CCC CTG         734
Glu Glu Leu Asn Ala Phe Gln Gln Lys Ser Cys Phe Gly His Pro Leu
            210                 215                 220
```

-continued

```
GCC CCG CAG GCC CTG GAG GAC GTG AAG ACG GTG GTG TGC AGG AAC GTG        782
Ala Pro Gln Ala Leu Glu Asp Val Lys Thr Val Val Cys Arg Asn Val
        225                 230                 235

GCG GGC GGC GTG CGG GAG GAC CGG CTG ACC CTG GAT GGT TTC CTC TTC        830
Ala Gly Gly Val Arg Glu Asp Arg Leu Thr Leu Asp Gly Phe Leu Phe
    240                 245                 250

CTG AAC ACG CTC TTC ATC CAG CGC GGC CGG CAC GAG ACC ACC TGG ACC        878
Leu Asn Thr Leu Phe Ile Gln Arg Gly Arg His Glu Thr Thr Trp Thr
255                 260                 265                 270

ATC CTG CGG CGC TTC GGC TAC AGC GAT GCC CTG GAG CTG ACT GCG GAC        926
Ile Leu Arg Arg Phe Gly Tyr Ser Asp Ala Leu Glu Leu Thr Ala Asp
                275                 280                 285

TAT CTC TCC CCT CTG ATC CAC GTG CCC CCC GGC TGC AGC ACG GAG CTC        974
Tyr Leu Ser Pro Leu Ile His Val Pro Pro Gly Cys Ser Thr Glu Leu
            290                 295                 300

AAC CAC CTT GGC TAC CAG TTT GTG CAG AGA GTG TTT GAG AAG CAC GAC       1022
Asn His Leu Gly Tyr Gln Phe Val Gln Arg Val Phe Glu Lys His Asp
        305                 310                 315

CAG GAC CGC GAC GGC GCC CTC TCG CCC GTG GAG CTG CAA AGC CTT TTC       1070
Gln Asp Arg Asp Gly Ala Leu Ser Pro Val Glu Leu Gln Ser Leu Phe
    320                 325                 330

AGT GTG TTC CCA GCA GCG CCC TGG GGC CCC GAG CTC CCA CGC ACA GTC       1118
Ser Val Phe Pro Ala Ala Pro Trp Gly Pro Glu Leu Pro Arg Thr Val
335                 340                 345                 350

CGC ACA GAG GCC GGC CGG TTG CCC CTG CAC GGA TAC CTC TGC CAG TGG       1166
Arg Thr Glu Ala Gly Arg Leu Pro Leu His Gly Tyr Leu Cys Gln Trp
                355                 360                 365

ACC CTG GTG ACC TAC CTG GAC GTC CGG AGC TGC CTT GGA CAC CTA GGC       1214
Thr Leu Val Thr Tyr Leu Asp Val Arg Ser Cys Leu Gly His Leu Gly
            370                 375                 380

TAC CTG GGC TAC CCC ACC CTC TGT GAG CAG GAC CAG GCC CAT GCC ATC       1262
Tyr Leu Gly Tyr Pro Thr Leu Cys Glu Gln Asp Gln Ala His Ala Ile
        385                 390                 395

ACA GTC ACT CGT GAG AAG AGG CTG GAC CAG GAG AAG GGA CAG ACG CAG       1310
Thr Val Thr Arg Glu Lys Arg Leu Asp Gln Glu Lys Gly Gln Thr Gln
    400                 405                 410

TGG AGC GTC CTC CTG TGC AAG GTG GTA GGG GCC CGT GGA GTG GGC AAG       1358
Trp Ser Val Leu Leu Cys Lys Val Val Gly Ala Arg Gly Val Gly Lys
415                 420                 425                 430

TCT GCC TTC CTG CAG GCC TTT CTC GGC CGC GGC CTG GGG CAC CAG GAC       1406
Ser Ala Phe Leu Gln Ala Phe Leu Gly Arg Gly Leu Gly His Gln Asp
                435                 440                 445

ACG AGG GAG CAG CCT CCC GGC TAC GCC ATC GAC ACG GTG CAG GTC AAT       1454
Thr Arg Glu Gln Pro Pro Gly Tyr Ala Ile Asp Thr Val Gln Val Asn
            450                 455                 460

GGA CAG GAG AAG TAC TTG ATC CTC TGT GAG GTG GGC ACA GAT GGT CTG       1502
Gly Gln Glu Lys Tyr Leu Ile Leu Cys Glu Val Gly Thr Asp Gly Leu
        465                 470                 475

CTG GCC ACA TCG CTG GAC GCC ACC TGT GAC GTT GCC TGC TTG ATG TTT       1550
Leu Ala Thr Ser Leu Asp Ala Thr Cys Asp Val Ala Cys Leu Met Phe
    480                 485                 490

GAT GGC AGT GAC CCA AAG TCC TTT GCA CAT TGT GCC AGC GTC TAC AAG       1598
Asp Gly Ser Asp Pro Lys Ser Phe Ala His Cys Ala Ser Val Tyr Lys
495                 500                 505                 510

CAC CAT TAC ATG GAC GGG CAG ACC CCC TGC CTC TTT GTC TCC TCC AAG       1646
His His Tyr Met Asp Gly Gln Thr Pro Cys Leu Phe Val Ser Ser Lys
                515                 520                 525

GCC GAC CTG CCC GAA GGT GTC GCG GTG TCT GGC CCA TCA CCG GCC GAG       1694
Ala Asp Leu Pro Glu Gly Val Ala Val Ser Gly Pro Ser Pro Ala Glu
            530                 535                 540
```

```
TTT TGC CGC AAG CAC CGG CTA CCC GCT CCC GTG CCG TTC TCC TGT GCT       1742
Phe Cys Arg Lys His Arg Leu Pro Ala Pro Val Pro Phe Ser Cys Ala
        545                 550                 555

GGC CCA GCC GAG CCC AGC ACC ACC ATC TTC ACC CAG CTC GCC ACC ATG       1790
Gly Pro Ala Glu Pro Ser Thr Thr Ile Phe Thr Gln Leu Ala Thr Met
        560                 565                 570

GCC GCC TTC CCA CAT TTG GTC CAC GCA GAG CTG CAT CCC TCT TCC TTC       1838
Ala Ala Phe Pro His Leu Val His Ala Glu Leu His Pro Ser Ser Phe
575                 580                 585                 590

TGG CTC CGG GGG CTG CTG GGG GTT GTC GGG GCC GCC GTG GCC GCA GTC       1886
Trp Leu Arg Gly Leu Leu Gly Val Val Gly Ala Ala Val Ala Ala Val
            595                 600                 605

CTC AGC TTC TCA CTC TAC AGG GTC CTG GTG AAG AGC CAG TGAGGCCCCT        1935
Leu Ser Phe Ser Leu Tyr Arg Val Leu Val Lys Ser Gln
            610                 615

GGTACCCAAG CCCCCTCCCC TGACCTGGGT GTGCCTCGCT GCTGGGGCTC TGCACTTTTT     1995

GTTTCTGAAG GCAGTCGATC TGCAGCGGGG CCTTATGCTG CCATGCACTG CCCTGGCTCC     2055

TGCCGGACCC CCAGGGTGGG CCGTGGCAGG TGGCTGAGCA GGAGCTCCCA AGTGCCGGCC     2115

ACCGCTGTCA GGGATTGCCC ACCCCTGGGC ATCATGTGTG TGGGGCCGGG GAGCACAGGT     2175

GTGGGAGCTG GTGACCCCAG ACCCAGAATT CTCAGGGCTC TACCCCCCTT TCCTGGTCCT     2235

AGGTGGCCAG TGGGTATGAG GAGGGCTGGA AGGCAGAGCT TTGGGCCAAA AGCAGGCGTT     2295

GGGGGGTCCC CCCTCAAGTT TGGAGCCGTT TCCGTGGTTG TAGCAGAGGA CCGGAGGTTG     2355

GGTTCCTGAT TAAACTTCAC TGTGTGTTTT CTATCTCGGA TCCCAGTCTC TGAAGACAAC     2415

TTGCTTTGAT TCAACCTAAA AAAAAAAAAA AAAAAAAAA A                          2456

(2) INFORMATION FOR SEQ ID NO:6:

(i) SEQUENCE CHARACTERISTICS:
        (A) LENGTH: 619 amino acids
        (B) TYPE: amino acid
        (D) TOPOLOGY: linear (ii) MOLECULE TYPE: protein (xi) SEQUENCE DESCRIPTION: SEQ ID NO:6:

Met Arg Arg Asp Val Arg Ile Leu Leu Leu Gly Glu Ala Gln Val Gly
 1               5                  10                  15

Lys Thr Ser Leu Ile Leu Ser Leu Val Gly Glu Glu Phe Pro Glu Glu
            20                  25                  30

Val Pro Pro Arg Ala Glu Glu Ile Thr Ile Pro Ala Asp Val Thr Pro
        35                  40                  45

Glu Lys Val Pro Thr His Ile Val Asp Tyr Ser Glu Ala Glu Gln Thr
    50                  55                  60

Asp Glu Glu Leu Arg Glu Glu Ile His Lys Ala Asn Val Val Cys Val
65                  70                  75                  80

Val Tyr Asp Val Ser Glu Glu Ala Thr Ile Glu Lys Ile Arg Thr Lys
                85                  90                  95

Trp Ile Pro Leu Val Asn Gly Gly Thr Thr Gln Gly Pro Arg Val Pro
            100                 105                 110

Ile Ile Leu Val Gly Asn Lys Ser Asp Leu Arg Ser Gly Ser Ser Met
        115                 120                 125

Glu Ala Val Leu Pro Ile Met Ser Gln Phe Pro Glu Ile Glu Thr Cys
    130                 135                 140

Val Glu Cys Ser Ala Lys Asn Leu Arg Asn Ile Ser Glu Leu Phe Tyr
```

```
145                 150                 155                 160
Tyr Ala Gln Lys Ala Val Leu His Pro Thr Ala Pro Leu Tyr Asp Pro
                165                 170                 175
Glu Ala Lys Gln Leu Arg Pro Ala Cys Ala Gln Ala Leu Thr Arg Ile
                180                 185                 190
Phe Arg Leu Ser Asp Gln Asp Leu Asp Gln Ala Leu Ser Asp Glu Glu
                195                 200                 205
Leu Asn Ala Phe Gln Lys Ser Cys Phe Gly His Pro Leu Ala Pro
    210                 215                 220
Gln Ala Leu Glu Asp Val Lys Thr Val Val Cys Arg Asn Val Ala Gly
225                 230                 235                 240
Gly Val Arg Glu Asp Arg Leu Thr Leu Asp Gly Phe Leu Phe Leu Asn
                245                 250                 255
Thr Leu Phe Ile Gln Arg Gly Arg His Glu Thr Thr Trp Thr Ile Leu
                260                 265                 270
Arg Arg Phe Gly Tyr Ser Asp Ala Leu Glu Leu Thr Ala Asp Tyr Leu
            275                 280                 285
Ser Pro Leu Ile His Val Pro Pro Gly Cys Ser Thr Glu Leu Asn His
    290                 295                 300
Leu Gly Tyr Gln Phe Val Gln Arg Val Phe Glu Lys His Asp Gln Asp
305                 310                 315                 320
Arg Asp Gly Ala Leu Ser Pro Val Glu Leu Gln Ser Leu Phe Ser Val
                325                 330                 335
Phe Pro Ala Ala Pro Trp Gly Pro Glu Leu Pro Arg Thr Val Arg Thr
                340                 345                 350
Glu Ala Gly Arg Leu Pro Leu His Gly Tyr Leu Cys Gln Trp Thr Leu
                355                 360                 365
Val Thr Tyr Leu Asp Val Arg Ser Cys Leu Gly His Leu Gly Tyr Leu
        370                 375                 380
Gly Tyr Pro Thr Leu Cys Glu Gln Asp Gln Ala His Ala Ile Thr Val
385                 390                 395                 400
Thr Arg Glu Lys Arg Leu Asp Gln Glu Lys Gly Gln Thr Gln Trp Ser
                405                 410                 415
Val Leu Leu Cys Lys Val Val Gly Ala Arg Gly Val Gly Lys Ser Ala
                420                 425                 430
Phe Leu Gln Ala Phe Leu Gly Arg Gly Leu Gly His Gln Asp Thr Arg
            435                 440                 445
Glu Gln Pro Pro Gly Tyr Ala Ile Asp Thr Val Gln Val Asn Gly Gln
    450                 455                 460
Glu Lys Tyr Leu Ile Leu Cys Glu Val Gly Thr Asp Gly Leu Leu Ala
465                 470                 475                 480
Thr Ser Leu Asp Ala Thr Cys Asp Val Ala Cys Leu Met Phe Asp Gly
                485                 490                 495
Ser Asp Pro Lys Ser Phe Ala His Cys Ala Ser Val Tyr Lys His His
            500                 505                 510
Tyr Met Asp Gly Gln Thr Pro Cys Leu Phe Val Ser Ser Lys Ala Asp
        515                 520                 525
Leu Pro Glu Gly Val Ala Val Ser Gly Pro Ser Pro Ala Glu Phe Cys
    530                 535                 540
Arg Lys His Arg Leu Pro Ala Pro Val Pro Phe Ser Cys Ala Gly Pro
545                 550                 555                 560
Ala Glu Pro Ser Thr Thr Ile Phe Thr Gln Leu Ala Thr Met Ala Ala
                565                 570                 575
```

-continued

```
Phe Pro His Leu Val His Ala Glu Leu His Pro Ser Ser Phe Trp Leu
            580             585                 590

Arg Gly Leu Leu Gly Val Val Gly Ala Ala Val Ala Ala Val Leu Ser
        595             600             605

Phe Ser Leu Tyr Arg Val Leu Val Lys Ser Gln
        610             615
```

MAMMALIAN PROTEINASES; OXIDOREDUCTASES; RELATED REAGENTS

This application is a divisional of commonly assigned, application No. 08/813,150, filed Mar. 7, 1997, now U.S. Pat. No. 6,069,229, which is incorporated herein by reference.

FIELD OF THE INVENTION

The present invention contemplates compositions related to proteins from animals, e.g., mammals, which function as proteinases; or oxidoreductases. In particular, it provides nucleic acids which encode, antibodies to, and proteins which exhibit biological functions, e.g., capacity to degrade proteinaceous substrates or serve as oxidoreductases.

BACKGROUND OF THE INVENTION

The proteases are a very broad group of enzymes which carry out an enzymatic function of hydrolysing a peptide bond. Within the group, there is a wide range of substrate specificities for the amino acids adjacent the cleavage sites. Proteases are typically categorized on the basis of their catalytic mecahnisms, e.g., based upon studies of their active sites, or by the effects of pH. Four main categories of proteases are serine proteinases, sulfhydryl proteases, acid proteases, and metalloproteases. They may also be classified according to their cleavage sites, e.g., endoproteases, amino peptidases, or carboxy peptidases.

Proteases have traditionally held a large share of the industrial enzyme market. Proteases are used in many industrial processes, including in detergents and cleaning products, e.g., to degrade protein materials such as blood and stains, in leather production, e.g., to remove hair, in baking, e.g., to break down glutens, in flavorings, e.g., soy sauce, in meat tenderizing, e.g., to break down collagen, in gelatin or food supplement production, in the textile industry, in waste treatment, and in the photographic industry. See, e.g., Gusek (1991) *Inform* 1:14–18; Zamost, et al. (1996) *J. Industrial Microbiol.* 8:71–82; James and Simpson (1996) *CRC Critical Reviews in Food Science and Nutrition* 36:437–463; Teichgraeber, et al. (1993) *Trends in Food Science and Technology* 4:145–149; Tjwan, et al. (1993) *J. Dairy Research* 60:269–286; Haard (1992) *J. Aquatic Food Product Technology* 1:17–35; van Dijk (1995) *Laundry and Cleaning News* 21:32–33; Nolte, et al. (1996) *J. Textile Institute* 87:212–226; Chikkodi, et al. (1995) *Textile Res. J.* 65:564–569; and Shih (1993) *Poultry Science* 72:1617–1620.

Oxidoreductases are involved in oxidation and reduction reactions, and have important functions, e.g., in oxidative phosphorylation. These enzymes are important in electron transport and general aerobic metabolism, and in many cases are associated with the mitochondrial membranes. In various circumstances, it may be useful to modulate oxidoreductase reactions to slow down or increase energy metabolism, e.g., in a cell or organ.

While there are many uses for proteases, there is always the need for a more active protease under various specific conditions. Similarly, regulation of oxidoreduction may be important. Alternatively, the distribution of these gene products may be useful as markers for specific cell or tissue types. There is a need for new proteinases or oxidoreductase enzymes of differing properties, specificities, and activities.

SUMMARY OF THE INVENTION

The present invention provides a binding compound comprising an antibody binding site which specifically binds to primate BS10.55 protein; or primate YTF03 protein; a nucleic acid comprising sequence encoding at least 12 amino acids of primate BS10.55 protein; or primate YTF03 protein; a substantially pure protein which is specifically recognized by the above antibody binding site; a substantially pure primate BS10.55, or primate YTF03 protein or peptide thereof; and a fusion protein comprising a 30 amino acid sequence portion of primate BS10. 55, or primate YTF03 protein sequence.

In certain binding compound embodiments, the antibody binding site is specifically immunoreactive with a protein selected from polypeptides of SEQ ID NO: 2 and 4; is raised against a purified or recombinantly produced primate BS10.55, or primate YTF3 protein; is immunoselected on a substantially purified or recombinantly produced primate BS10.55, or primate YTF03 protein; is in a monoclonal antibody, Fab, or F(ab)2; is detectably labeled; is attached to a solid substrate; is from a rabbit or mouse; binds with a Kd of at least about 300 mM; is fused to another protein segment; is in a chimeric antibody; or is coupled to another chemical moiety.

The invention also provides a method of making an antigen-antibody complex, comprising a step of contacting a primate biological sample to a specific binding antibody described. In preferred embodiments, the method further includes steps to purify the antigen or antibody.

Alternative embodiments provide an antibody binding site wherein the binding site is detected in a biological sample by a method comprising the steps of contacting a binding agent having an affinity for BS10.55 or YTF03 protein with the biological sample; incubating the binding agent with the biological sample to form a binding agent: BS10.55 or binding agent: YTF03 protein complex; and detecting the complex. In certain embodiments, the biological sample is human, and the binding agent is an antibody.

The invention also provides kits containing a composition described above and instructional material for the use of the composition; or segregation of the composition into a container. Typically, the kit is used to make a qualitative or quantitative analysis.

The invention also embraces a cell comprising an antibody described above; a cell transfected with a nucleic acid described above; or a cell comprising a fusion protein described above.

In nucleic acid embodiments, the nucleic acid may encode a polypeptide which specifically binds an antibody generated against an immunogen selected from the group consisting of the mature polypeptides of SEQ ID NO: 2 and 4. Alternatively, the nucleic acid may encode at least 12 amino acids of SEQ ID NO: 2 or SEQ ID NO: 4; comprise sequence of at least about 39 nucleotides selected from protein coding portions of SEQ ID NO: 1 or 3; hybridize to SEQ ID NO: 1 or 3 under stringent wash conditions of at least 45° C. and less than about 150 mM salt; comprise sequence made by a synthetic method; be an expression vector; be detectably labeled; be attached to a solid substrate; be from human; bind with a Kd of at least about 300 μM; be fused to another nucleic acid segment; be coupled to another chemical moiety; be operably associated with promoter, ribosome binding site, or poly-A addition site; be a PCR product; be transformed into a cell, including a bacterial cell; be in a sterile composition; be capable of selectively hybridizing to a nucleic acid encoding a BS10.55, or YTF03 protein; comprise a natural sequence; comprise a mature protein coding segment of SEQ ID NO: 1 or 3; encode proteolytically active portion of BS10.55;

encode an oxidoreductive active portion of YTF03; be detected in a biological sample by a method comprising: contacting a biological sample with a nucleic acid probe capable of selectively hybridizing to said nucleic acid, incubating the nucleic acid probe with the biological sample to form a hybrid of the nucleic acid probe with complementary nucleic acid sequences present in the biological sample; and determining the extent of hybridization of the nucleic acid probe to the complementary nucleic acid sequences, including the method where the nucleic acid probe is capable of hybridizing to a nucleic acid encoding a protein selected from the group consisting of the mature polypeptides of SEQ ID NO 2 and 4.

In protein or polypeptide embodiments, the proteins may bind with a Kd of at least about 30 µM to an antibody generated against an immunogen of the polypeptides of SEQ ID NO: 2 or 4; be immunoselected on an antibody which selectively binds a polypeptide of SEQ ID NO: 2 or 4; comprise sequence of at least 12 contiguous residues of SEQ ID NO: 2 or 4; exhibit a post-translational modification pattern distinct from natural BS10.55, or YTF03; be 3-fold or fewer substituted from natural sequence; be recombinantly produced; be denatured; have sequence of full length natural polypeptide; be detectably labeled; be attached to a solid substrate; be from human; be in a sterile composition; be fused to another protein segment; be coupled to another chemical moiety; comprise at least a fragment of at least 32 amino acid residues from a human BS10.55, or human YTF03 protein; comprise mature polypeptide sequence selected from the group consisting of SEQ ID NO 2 and 4; be a soluble protein; be a naturally occurring protein; be a proteolytically active portion of BS10.55; or be an oxidoreductive active portion of YTF03.

The invention also provides an isolated protein which specifically binds to an antibody generated against an immunogen selected from the group consisting of the full length polypeptides of SEQ ID NO: 2 or 4. Preferably such protein binds to the antibody with a Kd of at least about 300 µM; is immunoselected on an antibody which selectively binds a polypeptide of SEQ ID NO: 2 or 4; comprises sequence of at least 12 contiguous residues of SEQ ID NO: 2 or 4; exhibits a post-translational modification pattern distinct from natural BS10.55, or YTF03; is 3-fold or fewer substituted from natural sequence; is recombinantly produced; is denatured; has sequence of full length natural polypeptide; is detectably labeled; is attached to a solid substrate; is from human; is in a sterile composition; is fused to another protein segment; is coupled to another chemical moiety; comprises at least a fragment of at least 32 amino acid residues from a human BS10.55, or human YTF03 protein; comprises mature polypeptide sequence selected from the group consisting of SEQ ID NO 2 and 4; is a soluble protein; comprises a proteolytic activity of BS10.55; or comprises an oxidoreductive activity of YTF03.

In certain other embodiments, the invention embraces a fusion protein described above, which comprises sequence from an enzymatically active portion of SEQ ID NO: 2 or 4. Preferably such protein binds with a Kd of at least about 300 µM to an antibody generated against an immunogen having sequence of a polypeptide of SEQ ID NO. 2 or 4; is immunoselected on an antibody which selectively binds a polypeptide of SEQ ID NO: 2 or 4; comprises sequence of at least 12 contiguous residues of SEQ ID NO: 2 or 4; is recombinantly produced; is denatured; has sequence of full length natural polypeptide; is detectably labeled; is attached to a solid substrate; comprises sequence from human; is in a sterile composition; is fused to another protein segment; is coupled to another chemical moiety; comprises at least a fragment of at least 32 amino acid residues from a human BS10.55, or human YTF03 protein; comprises mature polypeptide sequence selected from the group consisting of SEQ ID NO 2 and 4; is a soluble protein; comprises a proteolytic activity of BS10.55; or comprises an oxidoreductive activity of YTF03.

The invention also provides a substantially pure protein described above which comprises a proteolytic activity of BS10.55; or an oxidoreductive activity of YTF03.

A method of modulating physiology or development of a cell comprising contacting said cell with said compositions is provided.

Likewise, the invention provides a binding compound comprising an antibody binding site which specifically binds to primate APD08; a nucleic acid comprising sequence encoding at least 12 amino acids of primate APD08; a substantially pure protein which is specifically recognized by the antibody binding site; a substantially pure primate APD08 protein or peptide thereof, and; a fusion protein comprising a 30 amino acid sequence portion of primate APD08 protein sequence.

DETAILED DESCRIPTION OUTLINE

I. General
II. Definitions
III. Nucleic Acids
IV. Making BS10.55 or YTF03 Protein
V. Antibodies; binding compounds
   a. antibody production
   b. immunoassays
VI. Purified BS10.55 and YTF03 Protein
VII. Physical Variants
VIII. Binding Agent: BS10.55 or YTF03 Protein Complexes
IX. Functional Variants
X. Uses
XI. Kits
XII. Substrate Identification

I. General

The present invention provides DNA sequences encoding mammalian proteins which exhibit structural properties or motifs characteristic of a protease; or an oxidoreductase. The proteins described herein are designated BS10.55 and YTF03. See Tables 1 and 2.

The descriptions below are directed, for exemplary purposes, to primate embodiments, e.g., human, but are likewise applicable to related embodiments from other, e.g., natural, sources. These sources should, where appropriate, include various vertebrates, typically warm blooded animals, e.g., birds and mammals, particularly domestic animals, and primates.

TABLE 1

Human BS10.55 nucleotide and predicted amino acid sequence.
SEQ ID NO: 1 and 2. The initiation methionine indicates one possible
start codon, though a second, perhaps more probable, initiation
codon encodes the methionine at position 14. A hydrophobic region
follows the latter, which may be a signal sequence running, e.g.,
to about Ala30; and a mature processed form may begin in the range
of 27–33, probably Ile31.

```
CGCCCGGGCA GGTGAGAAAT TGGAGAAGAT AAAACTGGAC ACTGGGGAGA CCACAACTTC    60

ATG CTG CGT GGG ATC TCC CAG CTA CCT GCA GTG GCC ACC ATG TCT TGG    108
Met Leu Arg Gly Ile Ser Gln Leu Pro Ala Val Ala Thr Met Ser Trp
 1           5                   10                  15

GTC CTG CTG CCT GTA CTT TGG CTC ATT GTT CAA ACT CAA GCA ATA GCC    156
Val Leu Leu Pro Val Leu Trp Leu Ile Val Gln Thr Gln Ala Ile Ala
            20                  25                  30

ATA AAG CAA ACA CCT GAA TTA ACG CTC CAT GAA ATA GTT TGT CCT AAA    204
Ile Lys Gln Thr Pro Glu Leu Thr Leu His Glu Ile Val Cys Pro Lys
        35                  40                  45

AAA CTT CAC ATT TTA CAC AAA AGA GAG ATC AAG AAC AAC CAG ACA GAA    252
Lys Leu His Ile Leu His Lys Arg Glu Ile Lys Asn Asn Gln Thr Glu
    50                  55                  60

AAG CAT GGC AAA GAG GAA AGG TAT GAA CCT GAA GTT CAA TAT CAG ATG    300
Lys His Gly Lys Glu Glu Arg Tyr Glu Pro Glu Val Gln Tyr Gln Met
65              70                  75                  80

ATC TTA AAT GGA GAA GAA ATC ATT CTC TCC CTA CAA AAA ACC AAG CAC    348
Ile Leu Asn Gly Glu Glu Ile Ile Leu Ser Leu Gln Lys Thr Lys His
                85                  90                  95

CTC CTG GGG CCA GAC TAC ACT GAA ACA TTG TAC TCA CCC AGA GGA GAG    396
Leu Leu Gly Pro Asp Tyr Thr Glu Thr Leu Tyr Ser Pro Arg Gly Glu
            100                 105                 110

GAA ATT ACC ACG AAA CCT GAG AAC ATG GAA CAC TGT TAC TAT AAA GGA    444
Glu Ile Thr Thr Lys Pro Glu Asn Met Glu His Cys Tyr Tyr Lys Gly
        115                 120                 125

AAC ATC CTA AAT GAA AAG AAT TCT GTT GCC AGC ATC AGT ACT TGT GAC    492
Asn Ile Leu Asn Glu Lys Asn Ser Val Ala Ser Ile Ser Thr Cys Asp
    130                 135                 140

GGG TTG AGA GGA TAC TTC ACA CAT CAT CAC CAA AGA TAC CAG ATA AAA    540
Gly Leu Arg Gly Tyr Phe Thr His His His Gln Arg Tyr Gln Ile Lys
145                 150                 155                 160

CCT CTG AAA AGC ACA GAC GAG AAA GAA CAT GCC GTC TTT ACA TCT AAC    588
Pro Leu Lys Ser Thr Asp Glu Lys Glu His Ala Val Phe Thr Ser Asn
                165                 170                 175

CAG GAG GAA CAA GAC CCA GCT AAC CAC ACA TGT GGT GTG AAG AGC ACT    636
Gln Glu Glu Gln Asp Pro Ala Asn His Thr Cys Gly Val Lys Ser Thr
            180                 185                 190

GAC GGG AAA CAA GGC CCA ATT CGA ATC TCT AGA TCA CTC AAA AGC CCA    684
Asp Gly Lys Gln Gly Pro Ile Arg Ile Ser Arg Ser Leu Lys Ser Pro
        195                 200                 205

GAG AAA GAA GAC TTT CTT CGG GCA CAG AAA TAC ATT GAT CTC TAT TTG    732
Glu Lys Glu Asp Phe Leu Arg Ala Gln Lys Tyr Ile Asp Leu Tyr Leu
    210                 215                 220

GTG CTG GAT AAT GCC TTT TAT AAG AAC TAT AAT GAG AAT CTA ACT CTG    780
Val Leu Asp Asn Ala Phe Tyr Lys Asn Tyr Asn Glu Asn Leu Thr Leu
225                 230                 235                 240

ATA AGA AGC TTT GTG TTT GAT GTG ATG AAC CTA CTC AAT GTG ATA TAT    828
Ile Arg Ser Phe Val Phe Asp Val Met Asn Leu Leu Asn Val Ile Tyr
                245                 250                 255

AAC ACC ATA GAT GTT CAA GTG GCC TTG GTA GGT ATG GAA ATC TGG TCT    876
Asn Thr Ile Asp Val Gln Val Ala Leu Val Gly Met Glu Ile Trp Ser
            260                 265                 270
```

TABLE 1-continued

Human BS10.55 nucleotide and predicted amino acid sequence.
SEQ ID NO: 1 and 2. The initiation methionine indicates one possible
start codon, though a second, perhaps more probable, initiation
codon encodes the methionine at position 14. A hydrophobic region
follows the latter, which may be a signal sequence running, e.g.,
to about Ala30; and a mature processed form may begin in the range
of 27–33, probably Ile31.

```
GAT GGG GAT AAG ATA AAG GTG GTG CCC AGC GCA AGC ACC ACG TTT GAC     924
Asp Gly Asp Lys Ile Lys Val Val Pro Ser Ala Ser Thr Thr Phe Asp
            275                 280                 285

AAC TTC CTG AGA TGG CAC AGT TCT AAC CCG GGG AAA AAG ATC CAC GAC     972
Asn Phe Leu Arg Trp His Ser Ser Asn Pro Gly Lys Lys Ile His Asp
        290                 295                 300

CAT GCT CAG CTT CTC AGC GGG ATT AGC TTC AAC AAT CGA CGT GTG GGA    1020
His Ala Gln Leu Leu Ser Gly Ile Ser Phe Asn Asn Arg Arg Val Gly
305                 310                 315                 320

CTG GCA GCT TCA AAT TCC TTG TGT TCC CCA TCT TCG GTT GCT GTT ATT    1068
Leu Ala Ala Ser Asn Ser Leu Cys Ser Pro Ser Ser Val Ala Val Ile
                325                 330                 335

GAG GCT AAA AAA AAG AAT AAT GTG GCT CTT GTA GGA GTG ATG TCA CAT    1116
Glu Ala Lys Lys Lys Asn Asn Val Ala Leu Val Gly Val Met Ser His
            340                 345                 350

GAG CTG GGC CAT GTC CTT GGT ATG CCT GAT GTT CCA TTC AAC ACC AAG    1164
Glu Leu Gly His Val Leu Gly Met Pro Asp Val Pro Phe Asn Thr Lys
        355                 360                 365

TGT CCC TCT GGC AGT TGT GTG ATG AAT CAG TAT CTG AGT TCA AAA TTC    1212
Cys Pro Ser Gly Ser Cys Val Met Asn Gln Tyr Leu Ser Ser Lys Phe
    370                 375                 380

CCA AAG GAT TTC AGT ACA TCT TGC CGT GCA CAT TTT GAA AGA TAC CTT    1260
Pro Lys Asp Phe Ser Thr Ser Cys Arg Ala His Phe Glu Arg Tyr Leu
385                 390                 395                 400

TTA TCT CAG AAA CCA AAG TGC CTG CTG CAA GCA CCT ATT CCT ACA AAT    1308
Leu Ser Gln Lys Pro Lys Cys Leu Leu Gln Ala Pro Ile Pro Thr Asn
                405                 410                 415

ATA ATG ACA ACA CCA GTG TGT GGG AAC CAC CTT CTA GAA GTG GGA GAA    1356
Ile Met Thr Thr Pro Val Cys Gly Asn His Leu Leu Glu Val Gly Glu
            420                 425                 430

GAC TGT GAT TGT GGC TCT CCT AAG GAG TGT ACC AGT CTC TGC TGT GAA    1404
Asp Cys Asp Cys Gly Ser Pro Lys Glu Cys Thr Ser Leu Cys Cys Glu
        435                 440                 445

GCC CTA ACG TGT AAA CTG AAG CCT GGA ACT GAT TGC GGA GGA GAT GCT    1452
Ala Leu Thr Cys Lys Leu Lys Pro Gly Thr Asp Cys Gly Gly Asp Ala
    450                 455                 460

CCA AAC CAT ACC ACA GAG TGA ATCCAAAGTC TGCTTCACTG AGATGCTACC       1503
Pro Asn His Thr Thr Glu  *
465                 470

TTGCCAGGAC AAGAACCAAG AACTCTAACT GTCCCAGGAA TCTTGTGAAT TTTCACCCAT  1563

AATGGTCTTT CACTTGTCAT TCTACTTTCT ATATTGTTAT CAGTCCAGGA AACAGGTAAA  1623

CAGATGTAAT TAGAGACATT GGCTCTTTGT TTAGGCCTAA TCTTTCTTTT TACTTTTTTT  1683

TTTCTTTTTT CTTTTTTTTT AAAGATCATG AATTTGTGAC TTAGTTCTGC CCTTTGGAGA  1743

ACAAAAGAAA GCAGTCTTCC ATCAAATCAC CTTAAAATGC ACGGCTAAAC TATTCAGAGT  1803

TAACACTCCA GAATTGTTAA ATTACAAGTA CTATGCTTTA ATGCTTCTTT CATCTTACTA  1863

GTATGGCCTA TAAAAAAAAT AATACCACTT GATGGGTGAA GGCTTTGGCA ATAGAAAGAA  1923

GAATAGAATT CAGGTTTTAT GTTATTCCTC TGTGTTCACT TCGCCTTGCT CTTGAAAGTG  1983

CAGTATTTTT CTACATCATG TCGAGAATGA TTCAATGTAA ATATTTTTCA TTTTATCATG  2043

TATATCCTAT ACACACATCT CCTTCATCAT CATATATGAA GTTTATTTTG AGAAGTCTAC  2103
```

TABLE 1-continued

Human BS10.55 nucleotide and predicted amino acid sequence.
SEQ ID NO: 1 and 2. The initiation methionine indicates one possible
start codon, though a second, perhaps more probable, initiation
codon encodes the methionine at position 14. A hydrophobic region
follows the latter, which may be a signal sequence running, e.g.,
to about Ala30; and a mature processed form may begin in the range
of 27–33, probably Ile31.

```
ATTGCTTACA TTTTAATTGA GCCAGCAAAG AAGGCTTAAT GATTTATTGA ACCATAATGT   2163

CAATAAAAAC ACAACTTTTG AGGCAAAAAA AAAAAAAAAA AAAAAAAAAA AAAAAAAAAA   2223

AAAAAAAAAA AAAAAAAAAG AAAAAAAAAA AAAAAAAAAA AAAGACCTGC CCGGGCG      2280
```

TABLE 2

Human YTF03 monoamine oxiase-like gene nucleic acid and predicted
amino acid sequence. SEQ ID NO: 3 and 4. The predicted signal
sequence would run, e.g., to about gln22; and a mature processed
form may begin in the range of 18–25, probably asp23. Putative
transmembrane segments run from about val62 to leu78; and ala272
to ala289. A mitochondrial localization motif is near gln22.

```
AGTGGAGAGG ACCGCGCTGT CCTGCTGTCA CCAAGAGCTG GAGACACCAT CTCCCACCGA    60

GAGTC ATG GCC CCA TTG GCC CTG CAC CTC CTC GTC CTC GTC CCC ATC      107
      Met Ala Pro Leu Ala Leu His Leu Leu Val Leu Val Pro Ile
        1               5                  10

CTC CTC AGC CTG GTG GCC TCC CAG GAC TGG AAG GCT GAA CGC AGC CAA    155
Leu Leu Ser Leu Val Ala Ser Gln Asp Trp Lys Ala Glu Arg Ser Gln
 15              20                  25                  30

GAC CCC TTC GAG AAA TGC ATG CAG GAT CCT GAC TAT GAG CAG CTG CTC    203
Asp Pro Phe Glu Lys Cys Met Gln Asp Pro Asp Tyr Glu Gln Leu Leu
                35                  40                  45

AAG GTG GTG ACC TGG GGG CTC AAT CGG ACC CTG AAG CCC CAG AGG GTG    251
Lys Val Val Thr Trp Gly Leu Asn Arg Thr Leu Lys Pro Gln Arg Val
            50                  55                  60

ATT GTG GTT GGC GCT GGT GTG GCC GGG CTG GTG GCC GCC AAG GTG CTC    299
Ile Val Val Gly Ala Gly Val Ala Gly Leu Val Ala Ala Lys Val Leu
            65                  70                  75

AGC GAT GCT GGA CAC AAG GTC ACC ATC CTG GAG GCA GAT AAC AGG ATC    347
Ser Asp Ala Gly His Lys Val Thr Ile Leu Glu Ala Asp Asn Arg Ile
     80                  85                  90

GGG GGC CGC ATC TTC ACC TAC CGG GAC CAG AAC ACG GGC TGG ATT GGG    395
Gly Gly Arg Ile Phe Thr Tyr Arg Asp Gln Asn Thr Gly Trp Ile Gly
 95                 100                 105                 110

GAG CTG GGA GCC ATG CGC ATG CCC AGC TCT CAC AGG ATC CTC CAC AAG    443
Glu Leu Gly Ala Met Arg Met Pro Ser Ser His Arg Ile Leu His Lys
                115                 120                 125

CTC TGC CAG GGC CTG GGG CTC AAC CTG ACC AAG TTC ACC CAG TAC GAC    491
Leu Cys Gln Gly Leu Gly Leu Asn Leu Thr Lys Phe Thr Gln Tyr Asp
                130                 135                 140

AAG AAC ACG TGG ACG GAG GTG CAC GAA GTG AAG CTG CGC AAC TAT GTG    539
Lys Asn Thr Trp Thr Glu Val His Glu Val Lys Leu Arg Asn Tyr Val
            145                 150                 155

GTG GAG AAG GTG CCC GAG AAG CTG GGC TAC GCC TTG CGT CCC CAG GAA    587
Val Glu Lys Val Pro Glu Lys Leu Gly Tyr Ala Leu Arg Pro Gln Glu
            160                 165                 170

AAG GGC CAC TCG CCC GAA GAC ATC TAC CAG ATG GCT CTC AAC CAG GCC    635
Lys Gly His Ser Pro Glu Asp Ile Tyr Gln Met Ala Leu Asn Gln Ala
175                 180                 185                 190
```

TABLE 2-continued

Human YTF03 monoamine oxiase-like gene nucleic acid and predicted
amino acid sequence. SEQ ID NO: 3 and 4. The predicted signal
sequence would run, e.g., to about gln22; and a mature processed
form may begin in the range of 18–25, probably asp23. Putative
transmembrane segments run from about val62 to leu78; and ala272
to ala289. A mitochondrial localization motif is near gln22.

| | | | | | | | | | | | | | | |
|---|---|---|---|---|---|---|---|---|---|---|---|---|---|---|
| CTC | AAA | GAC | CTC | AAG | GCA | CTG | GGC | TGC | AGA | AAG | GCG | ATG | AAG | AAG TTT | 683 |
| Leu | Lys | Asp | Leu | Lys | Ala | Leu | Gly | Cys | Arg | Lys | Ala | Met | Lys | Lys Phe | |
| | | | 195 | | | | 200 | | | | | 205 | | | |
| GAA | AGG | CAC | ACG | CTC | TTG | GAA | TAT | CTT | CTC | GGG | GAG | GGG | AAC | CTG AGC | 731 |
| Glu | Arg | His | Thr | Leu | Leu | Glu | Tyr | Leu | Leu | Gly | Glu | Gly | Asn | Leu Ser | |
| | | | 210 | | | | 215 | | | | | 220 | | | |
| CGG | CCG | GCC | GTG | CAG | CTT | CTG | GGA | GAC | GTG | ATG | TCC | GAG | GAT | GGC TTC | 779 |
| Arg | Pro | Ala | Val | Gln | Leu | Leu | Gly | Asp | Val | Met | Ser | Glu | Asp | Gly Phe | |
| | | | 225 | | | | 230 | | | | | 235 | | | |
| TTC | TAT | CTC | AGC | TTC | GCC | GAG | GCC | CTC | CGG | GCC | CAC | AGC | TGC | CTC AGC | 827 |
| Phe | Tyr | Leu | Ser | Phe | Ala | Glu | Ala | Leu | Arg | Ala | His | Ser | Cys | Leu Ser | |
| | | | 240 | | | | 245 | | | | | 250 | | | |
| GAC | AGA | CTC | CAG | TAC | AGC | CGC | ATC | GTG | GGT | GGC | TGG | GAC | CTG | CTG CCG | 875 |
| Asp | Arg | Leu | Gln | Tyr | Ser | Arg | Ile | Val | Gly | Gly | Trp | Asp | Leu | Leu Pro | |
| 255 | | | | 260 | | | | 265 | | | | | 270 | | |
| CGC | GCG | CTG | CTG | AGC | TCG | CTG | TCC | GGG | CTT | GTG | CTG | TTG | AAC | GCG CCC | 923 |
| Arg | Ala | Leu | Leu | Ser | Ser | Leu | Ser | Gly | Leu | Val | Leu | Leu | Asn | Ala Pro | |
| | | | | 275 | | | | 280 | | | | | 285 | | |
| GTG | GTG | GCG | ATG | ACC | CAG | GGA | CCG | CAC | GAT | GTG | CAC | GTG | CAG | ATC GAG | 971 |
| Val | Val | Ala | Met | Thr | Gln | Gly | Pro | His | Asp | Val | His | Val | Gln | Ile Glu | |
| | | | 290 | | | | 295 | | | | | 300 | | | |
| ACC | TCT | CCC | CCG | GCG | CGG | AAT | CTG | AAG | GTG | CTG | AAG | GCC | GAC | GTG GTG | 1019 |
| Thr | Ser | Pro | Pro | Ala | Arg | Asn | Leu | Lys | Val | Leu | Lys | Ala | Asp | Val Val | |
| | | | 305 | | | | 310 | | | | | 315 | | | |
| CTG | CTG | ACG | GCG | AGC | GGA | CCG | GCG | GTG | AAG | CGC | ATC | ACC | TTC | TCG CCG | 1067 |
| Leu | Leu | Thr | Ala | Ser | Gly | Pro | Ala | Val | Lys | Arg | Ile | Thr | Phe | Ser Pro | |
| | | | 320 | | | | 325 | | | | | 330 | | | |
| CCG | CTG | CCC | CGC | CAC | ATG | CAG | GAG | GCG | CTG | CGG | AGG | CTG | CAC | TAC GTG | 1115 |
| Pro | Leu | Pro | Arg | His | Met | Gln | Glu | Ala | Leu | Arg | Arg | Leu | His | Tyr Val | |
| 335 | | | | 340 | | | | 345 | | | | | 350 | | |
| CCG | GCC | ACC | AAG | GTG | TTC | CTA | AGC | TTC | CGC | AGG | CCC | TTC | TGG | CGC GAG | 1163 |
| Pro | Ala | Thr | Lys | Val | Phe | Leu | Ser | Phe | Arg | Arg | Pro | Phe | Trp | Arg Glu | |
| | | | | 355 | | | | 360 | | | | | 365 | | |
| GAG | CAC | ATT | GAA | GGC | GGC | CAC | TCA | AAC | ACC | GAT | CGC | CCG | TCG | CGC ATG | 1211 |
| Glu | His | Ile | Glu | Gly | Gly | His | Ser | Asn | Thr | Asp | Arg | Pro | Ser | Arg Met | |
| | | | 370 | | | | 375 | | | | | 380 | | | |
| ATT | TTC | TAC | CCG | CCG | CCG | CGC | GAG | GGC | GCG | CTG | CTG | CTG | GCC | TCG TAC | 1259 |
| Ile | Phe | Tyr | Pro | Pro | Pro | Arg | Glu | Gly | Ala | Leu | Leu | Leu | Ala | Ser Tyr | |
| | | 385 | | | | 390 | | | | | 395 | | | | |
| ACG | TGG | TCG | GAC | CCG | GCG | GCA | GCG | TTC | GCC | GGC | TTG | AGC | CGG | GAA GAG | 1307 |
| Thr | Trp | Ser | Asp | Pro | Ala | Ala | Ala | Phe | Ala | Gly | Leu | Ser | Arg | Glu Glu | |
| | | | 400 | | | | 405 | | | | | 410 | | | |
| GCG | TTG | CGC | TTG | GCG | CTC | GAC | GAC | GTG | GCG | GCA | TTG | CAC | GGG | CCT GTC | 1355 |
| Ala | Leu | Arg | Leu | Ala | Leu | Asp | Asp | Val | Ala | Ala | Leu | His | Gly | Pro Val | |
| 415 | | | | 420 | | | | 425 | | | | | 430 | | |
| GTG | CGC | CAG | CTC | TGG | GAC | GGC | ACC | GGC | GTC | GTC | AAG | CGT | TGG | GCG GAG | 1403 |
| Val | Arg | Gln | Leu | Trp | Asp | Gly | Thr | Gly | Val | Val | Lys | Arg | Trp | Ala Glu | |
| | | | | 435 | | | | 440 | | | | | 445 | | |
| GAC | CAG | CAC | AGC | CAG | GGT | GGC | TTT | GTG | GTA | CAG | CCG | CCG | GCG | CTC TGG | 1451 |
| Asp | Gln | His | Ser | Gln | Gly | Gly | Phe | Val | Val | Gln | Pro | Pro | Ala | Leu Trp | |
| | | | 450 | | | | 455 | | | | | 460 | | | |
| CAA | ACC | GAA | AAG | GAT | GAC | TGG | ACG | GTC | CCT | TAT | GGC | CGC | ATC | TAC TTT | 1499 |
| Gln | Thr | Glu | Lys | Asp | Asp | Trp | Thr | Val | Pro | Tyr | Gly | Arg | Ile | Tyr Phe | |
| | | | 465 | | | | 470 | | | | | 475 | | | |

TABLE 2-continued

Human YTF03 monoamine oxiase-like gene nucleic acid and predicted
amino acid sequence. SEQ ID NO: 3 and 4. The predicted signal
sequence would run, e.g., to about gln22; and a mature processed
form may begin in the range of 18–25, probably asp23. Putative
transmembrane segments run from about val62 to leu78; and ala272
to ala289. A mitochondrial localization motif is near gln22.

```
GCC GGC GAG CAC ACC GCC TAC CCG CAC GGC TGG GTG GAG ACG GCG GTC      1547
Ala Gly Glu His Thr Ala Tyr Pro His Gly Trp Val Glu Thr Ala Val
    480             485                 490

AAG TCG GCG CTG CGC GCC GCC ATC AAG ATC AAC AGC CGG AAG GGG CCT      1595
Lys Ser Ala Leu Arg Ala Ala Ile Lys Ile Asn Ser Arg Lys Gly Pro
495                 500                 505                 510

GCA TCG GAC ACG GCC AGC CCC GAG GGG CAC GCA TCT GAC ATG GAG GGG      1643
Ala Ser Asp Thr Ala Ser Pro Glu Gly His Ala Ser Asp Met Glu Gly
                515                 520                 525

CAG GGG CAT GTG CAT GGG GTG GCC AGC AGC CCC TCG CAT GAC CTG GCA      1691
Gln Gly His Val His Gly Val Ala Ser Ser Pro Ser His Asp Leu Ala
                530                 535                 540

AAG GAA GAA GGC AGC CAC CCT CCA GTC CAA GGC CAG TTA TCT CTC CAA      1739
Lys Glu Glu Gly Ser His Pro Pro Val Gln Gly Gln Leu Ser Leu Gln
        545                 550                 555

AAC ACG ACC CAC ACG AGG ACC TCG CAT TAA AGTATTTTCG G                 1780
Asn Thr Thr His Thr Arg Thr Ser His *
560                 565
```

The proteins of this invention are defined in part by their sequences, and by their physicochemical and biological properties. The biological properties of the human proteases described herein, e.g., human BS10.55, and oxidoreductases, e.g., human YTF03, are defined by their amino acid sequences, and mature sizes. They also should share certain biological enzymatic properties of their respective proteins.

The human protease YTF03 translation product exhibits structural motifs of a member of the metalloproteinase family of proteases, more specifically to a family of disintegrin-metalloproteinases. These proteins, in the latent form, typically possess a prodomain form which masks the catalytic site, which chelates a zinc ion. See Vallee and Auld (1990) Biochemistry 29:5647–5659. The processed mature protein is typically a potent cell-matrix degrading enzyme. See, e.g., Birkedal-Hansen (1990) Proc. Nat'l Acad. Sci. USA 87:5578–5582. Distinct from the family of strictly matrix-metalloproteinases (see, e.g., Birkedal-Hansen, et al. (1993) Crit. Rev. Oral. Biol. Med. 4:197–250), the disintegrin-metalloproteinases comprise, besides the zinc-chelating domain, a 90 amino acid disintegrin cysteine rich domain. See, e.g., Hite, et al. (1992) Biochemistry 31:6203–6211. This domain binds integrin cell adhesion molecules and can disrupt cell-matrix interactions. Gould, et al. (1990) Proc. Soc. Exp. Biol. Med. 195:168–171. It is postulated that the disintegrin moiety supports the catalytic domain in recognising and specifically cleaving matrix substrates. A large number of disintegrins are found in snake venoms, which inhibit platelet aggregation by competing with fibrinogen for binding to the platelet's glycoprotein IIb-IIa complex. The mammalian disintegrin-metalloproteinases include fertilin α (Blobel, et al. (1992) Nature 356:248–252), meltrin (Yagami-Hiromasa, et al. (1995) Nature 377:652–656), MS2 (Yoshida, et al. (1990) Int. Immunol. 2:585–591), EAP1 (Perry, et al. (1992) Biochem J. 286:671–675), and ADAMTS (Kuno, et al. (1997) J. Biol. Chem. 272:556–562). Fertilin α and meltrin are likely to be membrane proteins and are thought involved in cell-cell fusion via a fusion peptide similar to virus envelope proteins. EAP1 and MS2 also contain a transmembrane spanning region, and ADAMTS comprises thrombospondin motifs. Interestingly, MS2 seems specifically expressed by mouse macrophages but its function is unclear.

BS10.55 contains the zinc binding peptide consensus at residues 352–359 of SEQ ID NO: 2 (His-Glu-Met/Leu-Gly-His-X-X-Gly) and the disintegrin homology lies between SEQ ID NO: 2 residues 430–460 shortly before the end of the open reading frame. The peptide motif at residues 187–189 (Cys-Gly-Val) is characteristic of the prodomain (Hite, et al. (1992) Biochemistry 31:6203–6211). BS10.55 exhibits a hydrophobic region following the second methinone (at 14) at the 5' end of the cDNA sequence, likely to be a signal sequence. This, and the lack of a putative transmembrane region, suggest that this novel disintegrin-metalloproteinases is secreted. Natural substrates for the proteinase may be identified using standard methods. Substrate sequence specificity may be determined, and search for such sequences in databases may identify specific candidates for physiological substrates.

The YTF03 gene was initially found by analysis of clones isolated from germinal center dendritic cells. This cDNA is distantly related to a family of enzymes which include monamine oxidases (MOAs). These proteins are typically mitochondrial outer membrane proteins found in at least two forms and are tissue restricted to, e.g., certain neurons and astrocytes. They generally function to oxidatively deaminate, e.g., vasoactive and neuroactive amines, and are often targets for amphetamines. The YTF03 product does not have the key residues which covalently bind the classical MOA's FAD cofactor, and so it may not exhibit monamine oxidase activity itself. The protein is most closely related to a hypothesized protein from a cyanobacteria, but only slightly more so than to other MOAs. The predicted protein has a convincing leader sequence, though it may have characteristics which suggest association with intracellular membranous compartments like other MOAs. It is evident that the overall structure of the body of the ORF is very strongly conserved. Despite the relatively low homology with its relatives, there is little tolerance for addition/ deletion changes (+/−1 residue) in certain regions. This suggests an intricate structural mix of alpha helices and beta sheets. PCR analysis suggests that YTF03 mRNA is expressed mainly in Dendritic Cells (DC) and monocytes, and to a lesser extent in some T cells.

A comparison search versus the GenPep database gave closest match to the sequence ACCESSION 1001515 cyanobacterium Synechocystis sp. hypothetical protein. Viewing the structure, there is fairly believable conservation of helix/sheet paterns, though the cyano ORF has no leader and is a little shortened at the C-terminus.

One of skill will readily recognize that some sequence variations may be tolerated, e.g., conservative substitutions or positions remote from the critical helical structures and remote from the identified or consensus critial active site regions, without altering significantly the biological activity of each respective molecule.

BS10.55 or YTF03 proteins are present in specific cell types, e.g., dendritic cells, and the interaction of the protease with a substrate will be important for mediating various aspects of cellular physiology or development. The cellular types which express messages encoding APG02 and YTF03 suggest that signals important in cell differentiation and development are mediated by them. See, e.g., Gilbert (1991) *Developmental Biology* (3d ed.) Sinauer Associates, Sunderland, Mass.; Browder, et al. (1991) *Developmental Biology* (3d ed.) Saunders, Philadelphia, Pa.; Russo, et al. (1992) *Development: The Molecular Genetic Approach* Springer-Verlag, New York, N.Y.; and Wilkins (1993) *Genetic Analysis of Animal Development* (2d ed.) Wiley-Liss, New York, N.Y. In particular, the proteases may be necessary for the conversion of pro-proteins to proteins, e.g., cytokine or protein precursors to mature forms, or for proper immunological function, e.g., antigen processing and presentation.

II. Definitions

The term "binding composition" refers to molecules that bind with specificity to BS10.55 or YTF03, respectively, e.g., in an antibody-antigen interaction. However, other compounds, e.g., complex associated proteins, may also specifically associate with BS10.55 or YTF03 to the exclusion of other molecules. Typically, the association will be in a natural physiologically relevant protein-protein interaction, either covalent or non-covalent, and may include members of a multiprotein complex, including carrier compounds or dimerization partners. The molecule may be a polymer, or chemical reagent. A functional analog may be a protease with structural modifications, or may be a wholly unrelated molecule, e.g., which has a molecular shape which interacts with the appropriate substrate cleavage determinants.

The term "binding agent:BS10.55 or YTF03 protein complex", as used herein, refers to a complex of a binding agent and a BS10.55 or YTF03 protein that is formed by specific binding of the binding agent to the BS10.55 or YTF03 protein. Specific binding of the binding agent means that the binding agent has a specific binding site that recognizes a site on the BS10.55 or YTF03 protein, typically in the native conformation, but possibly in a denatured conformation, e.g., a Western blot. For example, antibodies raised to a BS10.55 or YTF03 protein and recognizing an epitope on the BS10.55 or YTF03 protein are capable of forming a binding agent:BS10.55 or binding agent:YTF03 protein complex by specific binding. Typically, the formation of a binding agent:BS10.55 or YTF03 protein complex allows the measurement of BS10.55 or YTF03 protein in a biological sample, e.g., a mixture with other proteins and biologics. The term "antibody:BS10.55 or antibody:YTF03 protein complex" refers to an embodiment in which the binding agent is an antibody. The antibody may be monoclonal, polyclonal, or a binding fragment of an antibody, e.g., an Fab, F(ab)2, or Fv fragment. The antibody will preferably be a polyclonal antibody for cross-reactivity determinations.

"Homologous" nucleic acid sequences, when compared, exhibit significant similarity or identity. The standards for homology in nucleic acids are either measures for homology generally used in the art by sequence comparison and/or phylogenetic relationship, or based upon hybridization conditions. Hybridization conditions are described in greater detail below.

An "isolated" nucleic acid is a nucleic acid, e.g., an RNA, DNA, or a mixed polymer, which is substantially separated from other biologic components which naturally accompany a native sequence, e.g., proteins and flanking genomic sequences from the originating species. The term embraces a nucleic acid sequence which has been removed from its naturally occurring environment, and includes recombinant or cloned DNA isolates and chemically synthesized analogs, or analogs biologically synthesized by heterologous systems. A substantially pure molecule includes isolated forms of the molecule. An isolated nucleic acid will usually contain homogeneous nucleic acid molecules, but will, in some embodiments, contain nucleic acids with minor sequence heterogeneity. This heterogeneity is typically found at the polymer ends or portions not critical to a desired biological function or activity.

As used herein, the term "BS10.55" or "YTF03" protein shall encompass, when used in a protein context, a protein having amino acid sequences, particularly from the protein motif portions, shown in SEQ ID NO: 2 or 4, respectively. In many contexts, a significant fragment of such a protein will be functionally equivalent. The invention also embraces a polypeptide which exhibits similar structure to human BS10.55 or YTF03 protein, e.g., which interacts with BS10.55 or YTF03 specific binding components. These binding components, e.g., antibodies, typically bind to BS10.55 or YTF03 protein with high affinity, e.g., at least about 100 nM, usually better than about 30 nM, preferably better than about 10 nM, and more preferably at better than about 3 nM.

The term "polypeptide" or "protein" as used herein includes a significant fragment or segment of protease motif portion of BS10.55 or YTF03 protein, and encompasses a stretch of amino acid residues of at least about 8 amino acids, generally at least about 10 amino acids, more generally at least about 12 amino acids, often at least about 14 amino acids, more often at least about 16 amino acids, typically at least about 18 amino acids, more typically at least about 20 amino acids, usually at least about 22 amino acids, more usually at least about 24 amino acids, preferably at least about 26 amino acids,more preferably at least about 28 amino acids, and, in particularly preferred embodiments, at least about 30 or more amino acids, e.g., 35, 40, 45, 50, 60, 70, 80, 100, etc.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any non-naturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

"Solubility" is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.) W. H. Freeman & Co., San Francisco, Calif.; and Cantor and Schimmel (1980) *Biophysical Chemistry* parts 1–3, W. H. Freeman & Co., San Francisco, Calif. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S. Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS (cholesteryl hemisuccinate) or CHAPS (3-[3-cholamidopropyl)-dimethylammonio]-1-propane sulfonate), or a low enough concentration as to avoid significant disruption of structural or physiological properties of the protein.

"Substantially pure" in a protein context typically means that the protein is isolated from other contaminating proteins, nucleic acids, and other biologicals derived from the original source organism. Purity, or "isolation" may be assayed by standard methods, and will ordinarily be at least about 50% pure, more ordinarily at least about 60% pure, generally at least about 70% pure, more generally at least about 80% pure, often at least about 85% pure, more often at least about 90% pure, preferably at least about 95% pure, more preferably at least about 98% pure, and in most preferred embodiments, at least 99% pure. Similar concepts apply, e.g., to antibodies or nucleic acids.

"Substantial similarity" in the nucleic acid sequence comparison context means either that the segments, or their complementary strands, when compared, are identical when optimally aligned, with appropriate nucleotide insertions or deletions, in at least about 50% of the nucleotides, generally at least about 56%, more generally at least about 59%, ordinarily at least about 62%, more ordinarily at least about 65%, often at least about 68%, more often at least about 71%, typically at least about 74%, more typically at least about 77%, usually at least about 80%, more usually at least about 85%, preferably at least about 90%, more preferably at least about 95 to 98% or more, and in particular embodiments, as high at about 99% or more of the nucleotides. Alternatively, substantial similarity exists when the segments will hybridize under selective hybridization conditions, to a strand, or its complement, typically using a sequence derived from SEQ ID NO: 1 or 3. Typically, selective hybridization will occur when there is at least about 55% similarity over a stretch of at least about 30 nucleotides, preferably at least about 65% over a stretch of at least about 25 nucleotides, more preferably at least about 75%, and most preferably at least about 90% over about 20 nucleotides. See Kanehisa (1984) *Nuc. Acids Res.* 12:203–213. The length of similarity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides, e.g., 150, 200, etc.

"Stringent conditions", in referring to homology or substantial similarity in the hybridization context, will be stringent combined conditions of salt, temperature, organic solvents, and other parameters, typically those controlled in hybridization reactions. The combination of parameters is generally more important than the measure of any single parameter. See, e.g., Wetmur and Davidson (1968) *J. Mol. Biol.* 31:349–370. A nucleic acid probe which binds to a target nucleic acid under stringent conditions is specific for said target nucleic acid. Such a probe is typically more than 11 nucleotides in length, and is sufficiently identical or complementary to a target nucleic acid over the region specified by the sequence of the probe to bind the target under stringent hybridization conditions.

BS10.55 or YTF03 proteins from other mammalian species can be cloned and isolated by cross-species hybridization of closely related species. See, e.g., below. Similarity may be relatively low between distantly related species, and thus hybridization of relatively closely related species is advisable. Alternatively, preparation of an antibody preparation which exhibits less species specificity may be useful in expression cloning approaches.

The phrase "specifically binds to an antibody" or "specifically immunoreactive with", when referring to a protein or peptide, refers to a binding reaction which is determinative of the presence of the protein in the presence of a heterogeneous population of proteins and other biological components. Thus, under designated immunoassay conditions, the specified antibodies bind to a particular protein and do not significantly bind other proteins present in the sample. Specific binding to an antibody under such conditions may require an antibody that is selected for its specificity for a particular protein. For example, antibodies raised to the human BS10.55 or YTF03 protein immunogen with the amino acid sequence depicted in SEQ ID NO: 2 or 4 can be selected by immunoaffinity or similar methods to obtain antibodies specifically immunoreactive with BS10.55 or YTF03 proteins and not with other proteins.

III. Nucleic Acids

BS10.55 or YTF03 proteins are exemplary of larger classes of structurally and functionally related proteins. The BS10.55 proteins will typically serve to cleave or process various proteins produced or processed by various cell types, e.g., for antigen presentation. The preferred embodiments, as disclosed, will be useful in standard procedures to isolate genes from different individuals or other species, e.g., warm blooded animals, such as birds and mammals. Cross hybridization will allow isolation of related genes encoding proteins from individuals, strains, or species. A number of different approaches are available to successfully isolate a suitable nucleic acid clone based upon the information provided herein. Southern blot hybridization studies can qualitatively determine the presence of homologous genes in human, monkey, rat, dog, cow, and rabbit genomes under specific hybridization conditions.

Complementary sequences will also be used as probes or primers. Based upon identification of the likely amino terminus, other peptides should be particularly useful, e.g., coupled with anchored vector or poly-A complementary PCR techniques or with complementary DNA of other peptides.

Techniques for nucleic acid manipulation of genes encoding BS10.55 or YTF03 proteins, such as subcloning nucleic acid sequences encoding polypeptides into expression vectors, labelling probes, DNA hybridization, and the like are described generally in Sambrook, et al. (1989) *Molecular Cloning: A Laboratory Manual* (2nd ed.) Vol. 1–3, Cold Spring Harbor Laboratory, Cold Spring Harbor Press, N.Y., which is incorporated herein by reference. This manual is hereinafter referred to as "Sambrook, et al.".

There are various methods of isolating DNA sequences encoding BS10.55 or YTF03 proteins. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed. Such probes can be used directly in hybridization assays to isolate DNA encoding BS10.55 or YTF03 proteins, or probes can be designed for use in amplification techniques such as PCR, for the isolation of DNA encoding BS10.55 or YTF03 proteins.

To prepare a cDNA library, mRNA is isolated from cells, preferably which express high levels of a BS10.55 or YTF03 protein. cDNA is prepared from the mRNA and ligated, e.g., into a recombinant vector. The vector is transfected into a recombinant host for propagation, screening, and cloning. Methods for making and screening cDNA libraries are well known. See Gubler and Hoffman (1983) *Gene* 25:263–269 and Sambrook, et al.

For a genomic library, the DNA can be extracted from tissue, and often either mechanically sheared or enzymatically digested to yield fragments of about 12–20 kb. The fragments are then separated by gradient centrifugation and cloned in bacteriophage lambda vectors. These vectors and phage are packaged in vitro, as described in Sambrook, et al. Recombinant phage are analyzed by plaque hybridization as described in Benton and Davis (1977) *Science* 196:180–182. Colony hybridization is carried out as generally described in, e.g., Grunstein, et al. (1975) *Proc. Natl. Acad. Sci. USA*. 72:3961–3965.

DNA encoding a BS10.55 or YTF03 protein can be identified in either cDNA or genomic libraries by its ability to hybridize with the nucleic acid probes described herein, e.g., in colony or plaque hybridization assays. The corresponding DNA regions are isolated, e.g., by standard methods familiar to those of skill in the art. See, e.g., Sambrook, et al.

Various methods of amplifying target sequences, such as the polymerase chain reaction, can also be used to prepare DNA encoding BS10.55 or YTF03 proteins. Polymerase chain reaction (PCR) technology may be used to amplify such nucleic acid sequences directly from mRNA, from cDNA, and/or from genomic libraries or cDNA libraries. The isolated sequences encoding BS10.55 or YTF03 proteins may also be used as templates for PCR amplification.

Typically, in PCR techniques, oligonucleotide primers complementary to two flanking regions in the DNA region to be amplified are synthesized. The polymerase chain reaction is then carried out using the two primers. See Innis, et al. (eds.) (1990) *PCR Protocols: A Guide to Methods and Applications* Academic Press, San Diego, Calif. Primers can be selected to amplify the entire regions encoding a full-length human BS10.55 or YTF03 protein or to amplify smaller DNA segments, as desired. Once such regions are PCR-amplified, they can be sequenced and oligonucleotide probes can be prepared from sequence obtained using standard techniques. These probes can then be used to isolate DNA's encoding BS10.55 or YTF03 proteins.

Oligonucleotides for use as probes are usually chemically synthesized according to the solid phase phosphoramidite triester method first described by Beaucage and Carruthers (1983) *Tetrahedron Lett.* 22(20): 1859–1862, or using an automated synthesizer, as described in Needham-VanDevanter, et al. (1984) *Nucleic Acids Res.* 12:6159–6168. Purification of oligonucleotides is performed e.g., by native acrylamide gel electrophoresis or by anion-exchange HPLC as described in Pearson and Regnier (1983) *J. Chrom.* 255:137–149. The sequence of the synthetic oligonucleotide can be verified using, e.g., the chemical degradation method of Maxam, A. M. and Gilbert, W. in Grossman, L. and Moldave (eds.) (1980) *Methods in Enzymology* 65:499–560 Academic Press, New York.

An isolated nucleic acid encoding a human BS10.55 or YTF03 protein was identified. The nucleotide sequence, corresponding open reading frames, and mature peptides are provided in Tables 1 or and SEQ ID NO: 1–4.

This invention provides isolated DNA or fragments to encode a BS10.55 or YTF03 protein or specific fragment thereof. In addition, this invention provides isolated or recombinant DNA which encodes a protein or polypeptide, and which is capable of hybridizing under appropriate conditions, e.g., high stringency, with the DNA sequences described herein. Said biologically active protein or polypeptide can be a functional protease or oxidoreductase segment, or fragment, and have an amino acid sequence as disclosed in SEQ ID NO: 2 or 4. Preferred embodiments will be full length natural sequences, from isolates, or proteolytic fragments thereof. Further, this invention contemplates the use of isolated or recombinant DNA, or fragments thereof, which encode proteins which exhibit high measures of identity to a BS10.55 or YTF03 protein, or which were isolated, e.g., using cDNA encoding a BS10.55 protease or YTF03 oxidoreductase protein as a probe. The isolated DNA can have the respective regulatory sequences in the 5' and 3' flanks, e.g., promoters, enhancers, poly-A addition signals, and others.

IV. Making Human BS10.55 or YTF03 Proteins

DNAs which encode a BS10.55 or YTF03 protein, or fragments thereof, can be obtained by chemical synthesis, screening cDNA libraries, or by screening genomic libraries prepared from a wide variety of cell lines or tissue samples.

These DNAs can be expressed in a wide variety of host cells for the synthesis of a full-length protein or fragments which can in turn, e.g., be used to generate polyclonal or monoclonal antibodies; for binding studies; for construction and expression of modified molecules; and for structure/function studies. Each of BS10.55 or YTF03, or their fragments, can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, e.g., BS10.55 or YTF03, or portions thereof, may be expressed as fusions with other proteins or possessing an epitope tag.

Expression vectors are typically self-replicating DNA or RNA constructs containing the desired antigen gene or its fragments, usually operably linked to appropriate genetic control elements that are recognized in a suitable host cell. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently from the host cell.

The vectors of this invention contain DNAs which encode a BS10.55 or YTF03 protein, or a significant fragment thereof, typically encoding, e.g., a biologically active polypeptide, or protein. The DNA can be under the control of a viral promoter and can encode a selection marker. This invention further contemplates use of such expression vectors which are capable of expressing eukaryotic cDNA coding for a BS10.55 or YTF03 protein in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of a BS10.55 or YTF03 protein gene or its fragments into the host DNA by recombination, or to integrate a promoter which controls expression of an endogenous gene.

Vectors, as used herein, contemplate plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector, but many other forms of vectors which serve an equivalent function are suitable for use herein. See, e.g., Pouwels, et al. (1985 and Supplements) *Cloning Vectors: A Laboratory Manual* Elsevier, N.Y.; and Rodriquez, et al. (eds.) (1988) *Vectors: A Survey of Molecular Cloning Vectors and Their Uses* Buttersworth, Boston, Mass.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or its derivatives. Vectors that can be used to express BS10.55 or YTF03 proteins or fragments thereof include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses* 10:205–236 Buttersworth, Boston, Mass.

Lower eukaryotes, e.g., yeasts and Dictyostelium, may be transformed with BS10.55- or YTF03- protein sequence containing vectors. For purposes of this invention, the most common lower eukaryotic host is the baker's yeast, Saccharomyces cerevisiae. It will be used generically to represent lower eukaryotes although a number of other strains and species will be essentially equivalent. Yeast vectors typically consist of a replication origin (unless of the integrating type), one or more selection genes, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series), integrating types (such as the YIp-series), or mini-chromosomes (such as the YCp-series).

Higher eukaryotic tissue culture cells are typically the preferred host cells for expression of the functionally active BS10.55 protease or YTF03 oxidoreductase proteins. In principle, many higher eukaryotic tissue culture cell lines may be used, e.g., insect baculovirus expression systems, whether from an invertebrate or vertebrate source. However, mammalian cells are preferred to achieve proper natural processing, both cotranslationally and posttranslationally. Transformation or transfection and propagation of such cells are routine. Useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (e.g., if genomic. DNA is used), a polyadenylation site, and a transcription termination site. These vectors also may contain selection and/or amplification genes. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610.

It is likely that BS10.55 or YTF03 protein need not be glycosylated to elicit biological responses. However, it will occasionally be desirable to express a BS10.55 or YTF03 polypeptide in a system which provides a specific or defined glycosylation pattern. In this case, the usual pattern will be that provided naturally by the expression system. However, the pattern will be modifiable by exposing the polypeptide, e.g., in unglycosylated form, to appropriate glycosylating proteins introduced into a heterologous expression system. For example, a BS10.55 or YTF03 protein gene may be co-transformed with one or more genes encoding mammalian or other glycosylating enzymes. It is further understood that over glycosylation may be detrimental to BS10.55 or YTF03 protein biological activity, and that one of skill may perform routine testing to optimize the degree of glycosylation which confers optimal biological activity.

A BS10.55 or YTF03 protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochem. Biophys. Acta* 988:427–454; Tse, et al. (1985) *Science* 230:1003–1008; and Brunner, et al. (1991) *J. Cell Biol.* 114:1275–1283.

Now that BS10.55 or YTF03 proteins have been characterized, fragments or derivatives thereof can be prepared by conventional processes for synthesizing peptides. These include processes such as are described in Stewart and Young (1984) *Solid Phase Peptide Synthesis* Pierce Chemical Co., Rockford, Ill.; Bodanszky and Bodanszky (1984) *The Practice of Peptide Synthesis* Springer-Verlag, New York, N.Y.; Bodanszky (1984) *The Principles of Peptide Synthesis* Springer-Verlag, New York, N.Y.; and Dawson, et al. (1994) *Science* 266:776–779. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The prepared protein and fragments thereof can be isolated and purified from the reaction mixture by means of peptide separation, for example, by extraction, precipitation, electrophoresis and various forms of chromatography, and the like. The BS10.55 or YTF03 proteins of this invention can be obtained in varying degrees of purity depending upon its desired use. Purification can be accomplished by use of known protein purification techniques or by the use of the antibodies or binding partners herein described, e.g., in immunoabsorbant affinity chromatography. This immunoabsorbant affinity chromatography is carried out, e.g., by first linking the antibodies to a solid support and then contacting the linked antibodies with solubilized lysates of appropriate source cells, lysates of other cells expressing the ligand, or lysates or supernatants of cells producing the BS10.55 or YTF03 proteins as a result of recombinant DNA techniques, see below.

Multiple cell lines may be screened for one which expresses a BS10.55 or YTF03 polypeptide or protein at a high level compared with other cells. Various cell lines, e.g., a mouse thymic stromal cell line TA4, is screened and selected for its favorable handling properties. Natural BS10.55 or YTF03 proteins can be isolated from natural sources, or by expression from a transformed cell using an appropriate expression vector. Purification of the expressed protein is achieved by standard procedures, or may be combined with engineered means for effective purification at high efficiency from cell lysates or supernatants. Epitope or other tags, e.g., FLAG or $His_6$ segments, can be used for such purification features.

V. Antibodies

Antibodies can be raised to various BS10.55 or YTF03 proteins, including individual, polymorphic, allelic, strain, or species variants, and fragments thereof, both in their naturally occurring (full-length) forms and in their recombinant forms. Additionally, antibodies can be raised to BS10.55 or YTF03 proteins in either their native (or active) forms or in their inactive, e.g., denatured, forms. Anti-idiotypic antibodies may also be used.

A. Antibody Production

A number of immunogens may be used to produce antibodies specifically reactive with BS10.55 or YTF03 proteins. Recombinant protein is a preferred immunogen for the production of monoclonal or polyclonal antibodies. Naturally occurring protein may also be used either in pure or impure form. Synthetic peptides, made using the human BS10.55 or YTF03 protein sequences described herein, may also used as an immunogen for the production of antibodies to BS10.55 or YTF03 proteins. Recombinant protein can be expressed in eukaryotic or prokaryotic cells as described herein, and purified as described. Naturally folded or denatured material can be used, as appropriate, for producing antibodies. Either monoclonal or polyclonal antibodies may be generated, e.g., for subsequent use in immunoassays to measure the protein.

Methods of producing polyclonal antibodies are well known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the BS10.55 or YTF03 protein of interest. For example, when appropriately high titers of antibody to the immunogen are obtained, usually after repeated immunizations, blood is collected from the animal and antisera are prepared. Further fractionation of the antisera to enrich for antibodies reactive to the protein can be done if desired. See, e.g., Harlow and Lane; or Coligan.

Monoclonal antibodies may be obtained by various techniques familiar to those skilled in the art. Typically, spleen cells from an animal immunized with a desired antigen are immortalized, commonly by fusion with a myeloma cell (see, Kohler and Milstein (1976) *Eur. J. Immunol.* 6:511–519, incorporated herein by reference). Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies' produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275–1281.

Antibodies, including binding fragments and single chain versions, against predetermined fragments of BS10.55 or YTF03 proteins can be raised by immunization of animals with conjugates of the fragments with carrier proteins as described above. Monoclonal antibodies are prepared from cells secreting the desired antibody. These antibodies can be screened for binding to normal or defective BS10.55 or YTF03 protein, or screened for agonistic or antagonistic activity, e.g., mediated through a receptor. These monoclonal antibodies will usually bind to normal or defective BS10.55 or YTF03, or fragments thereof, with at least a $K_D$ of about 1 mM, more usually at least about 300 $\mu$M, typically at least about 10 $\mu$M, more typically at least about 30 $\mu$M, preferably at least about 10 $\mu$M, and more preferably at least about 3 $\mu$M or better.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256:495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see, Cabilly, U.S. Pat. No. 4,816,567; and Queen, et al. (1989) *Proc. Nat'l Acad. Sci. USA* 86:10029–10033; or made in transgenic mice, see Mendez, et al. (1997) *Nature Genetics* 15:146–156.

The antibodies of this invention are useful for affinity chromatography in isolating BS10.55 or YTF03 protein. Columns can be prepared where the antibodies are linked to a solid support, e.g., particles, such as AGAROSE (Amersham Pharmacia Biotech, Piscataway, N.J.), SEPHADEX (Amersham Pharmacia Biotech, Piscataway, N.J.), or the like, where a cell lysate or supernatant may be passed through the column, the column washed, followed by increasing concentrations of a mild denaturant, whereby purified BS10.55 or YTF03 protein will be released. The converse can be performed using protein to isolate specific antibodies.

Other antibodies may block enzymatic activity. The antibodies may also be used to screen expression libraries for particular expression products. Usually the antibodies used in such a procedure will be labeled with a moiety allowing easy detection of presence of antigen by antibody binding.

Antibodies to BS10.55 or YTF03 proteins may be used for the identification of cell populations expressing BS10.55 or YTF03 protein. By assaying the expression products of cells expressing BS10.55 or YTF03 proteins it is possible to diagnose disease, e.g., metabolic conditions. The proteins may also be markers for specific tissue or cell subpopulations, e.g., dendritic cells.

Antibodies raised against each BS10.55 or YTF03 protein will also be useful to raise anti-idiotypic antibodies. These will be useful in detecting or diagnosing various immunological conditions related to expression of the respective antigens.

B. Immunoassays

A particular protein can be measured by a variety of immunoassay methods. For a review of immunological and immunoassay procedures in general, see Stites and Terr (eds.) (1991) *Basic and Clinical Immunology* (7th ed.). Moreover, the immunoassays of the present invention can be performed in many configurations, which are reviewed extensively in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B. V., Amsterdam; and Harlow and Lane *Antibodies. A Laboratory Manual*, supra, each of which is incorporated herein by reference. See also Chan (ed. 1987) *Immunoassay: A Practical Guide* Academic Press, Orlando, Fla.; Price and Newman (eds. 1991) *Principles and Practice of Immunoassays* Stockton Press, NY, and Ngo (ed. 1988) *Non-isotopic Immunoassays* Plenum Press, NY.

Immunoassays for measurement of BS10.55 or YTF03 proteins or peptides can be performed by a variety of methods known to those skilled in the art. In brief, immunoassays to measure the protein can be either competitive or noncompetitive binding assays. In competitive binding assays, the sample to be analyzed competes with a labeled analyte for specific binding sites on a capture agent bound to a solid surface. Preferably the capture agent is an antibody specifically reactive with BS10.55 or YTF03 proteins produced as described above. The concentration of labeled analyte bound to the capture agent is inversely proportional to the amount of free analyte present in the sample.

In a competitive binding immunoassay, the BS10.55 or YTF03 protein present in the sample competes with labeled protein for binding to a specific binding agent, for example, an antibody specifically reactive with the BS10.55 or YTF03 protein. The binding agent may be bound to a solid surface to effect separation of bound labeled protein from the unbound labeled protein. Alternately, the competitive binding assay may be conducted in liquid phase and a variety of techniques known in the art may be used to separate the bound labelled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

BS10.55 or YTF03 proteins may also be determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of BS10.55 or YTF03 proteins in a sample. Electrophoresis is carried out, for example, on a tissue sample suspected of containing the protein. Following electrophoresis to separate the proteins, and transfer of the proteins to a suitable solid support, e.g., a nitrocellulose filter, the solid support is incubated with an antibody reactive with the protein. This antibody may be labeled, or alternatively may be detected by subsequent incubation with a second labeled antibody that binds the primary antibody.

The immunoassay formats described above may employ labeled assay components. The label may be coupled directly or indirectly to the desired component of the assay according to methods well known in the art. A wide variety of labels and methods may be used. Traditionally, a radioactive label incorporating $^3$H, $^{125}$I, $^{35}$S, $^{14}$C, or $^{32}$P was used. Non-radioactive labels include ligands which bind to labeled antibodies, fluorophores, chemiluminescent agents, enzymes, and antibodies which can serve as specific binding pair members for a labeled ligand. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see Stites and Terr (eds.) *Basic and Clinical Immunology* (7th ed.) supra; Maggio (ed.) *Enzyme Immunoassay*, supra; and Harlow and Lane *Antibodies. A Laboratory Manual*, supra.

In brief, immunoassays to measure antisera reactive with BS10.55 or YTF03 proteins can be either competitive or noncompetitive binding assays. In competitive binding assays, the sample analyte competes with a labeled analyte for specific binding sites on a capture agent bound to a solid surface. Preferably the capture agent is a purified recombinant BS10.55 or YTF03 protein produced as described above. Other sources of BS10.55 or YTF03 proteins, including isolated or partially purified naturally occurring protein, may also be used. Noncompetitive assays include sandwich assays, in which the sample analyte is bound between two analyte-specific binding reagents. One of the binding agents is used as a capture agent and is bound to a solid surface. The second binding agent is labeled and is used to measure or detect the resultant complex by visual or instrument means. A number of combinations of capture agent and labelled binding agent can be used. A variety of different immunoassay formats, separation techniques, and labels can be also be used similar to those described above for the measurement of BS10.55 or YTF03 proteins. Similar methods may be used to evaluate or quantitate specific binding compounds.

VI. Purified BS10.55 or YTF03 proteins

Human BS10.55 or YTF03 protein amino acid sequences are provided in SEQ ID NO: 2 and 4.

Purified protein or defined peptides are useful for generating antibodies by standard methods, as described above. Synthetic peptides or purified protein can be presented to an immune system to generate polyclonal and. monoclonal antibodies. See, e.g., Coligan (1991) *Current Protocols in Immunology* Wiley/Greene, N.Y.; and Harlow and Lane (1989) *Antibodies: A Laboratory Manual* Cold Spring Harbor Press, NY, which are incorporated herein by reference.

The specific binding composition can be used for screening an expression library made from a cell line which expresses a BS10.55 or YTF03 protein. Many methods for screening are available, e.g., standard staining of surface expressed ligand, or by panning. Screening of intracellular expression can also be performed by various staining or immunofluorescence procedures. The binding compositions could be used to affinity purify or sort out cells expressing the ligand.

The peptide segments, along with comparison to homologous genes, can also be used to produce appropriate oligonucleotides to screen a library. The genetic code can be used to select appropriate oligonucleotides useful as probes for screening. In combination with polymerase chain reaction (PCR) techniques, synthetic oligonucleotides will be useful in selecting desired clones from a library, including natural allelic and polymorphic variants.

The peptide sequences allow preparation of peptides to generate antibodies to recognize such segments, and allow preparation of oligonucleotides which encode such sequences. The sequence also allows for synthetic preparation, e.g., see Dawson, et al. (1994) *Science* 266:776–779. Analysis of the structural features in comparison with the most closely related reported sequences has revealed similarities with other proteins, particularly the class of proteins known as proteases or oxidoreductases.

VII. Physical Variants

This invention also encompasses proteins or peptides having substantial amino acid sequence similarity with an amino acid sequence of a BS10.55 or YTF03 protein. Natural variants include individual, polymorphic, allelic, strain, or species variants. Conservative substitutions in the amino acid sequence will normally preserve most relevant biological activities. In particular, various substitutions can be made, e.g., embodiments with 10-fold substitutions, 7-fold substitutions, 5-fold substitutions, 3-fold substitutions, 2-fold, and etc. Such embodiments will typically retain particular features, e.g., antigenicity, with the natural forms.

Amino acid sequence similarity, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences include natural polymorphic, allelic, and interspecies variations in each respective protein sequence. Typical homologous proteins or peptides will have from 50–100% similarity (if gaps can be introduced), to 75–100% similarity (if conservative substitutions are included) with the amino acid sequence of the BS10.55 or. YTF03 protein. Similarity measures will be at least about 50%, generally at least about 60%, more generally at least about 65%, usually at least about 70%, more usually at least about 75%, preferably at least about 80%, and more preferably at least about 80%, and in particularly preferred embodiments, at least about 85% or more. See also Needleham, et al. (1970) *J. Mol. Biol.* 48:443–453; Sankoff, et al. (1983) *Time Warps. String Edits, and Macromolecules: The Theory and Practice of Sequence Comparison* Chapter One, Addison-Wesley, Reading, Mass.; and software packages from IntelliGenetics, Mountain View, Calif.; and the University of Wisconsin Genetics Computer Group, Madison, Wis.

Natural nucleic acids encoding mammalian BS10.55 or YTF03 proteins will typically hybridize to the nucleic acid sequence of SEQ ID NO: 1 or 3 under stringent conditions. For example, nucleic acids encoding human BS10.55 or YTF03 proteins will normally hybridize to the nucleic acid of SEQ ID NO: 1 or 3 under stringent hybridization conditions. Generally, stringent conditions are selected to be about 10° C. lower than the thermal melting point (Tm) for the probe sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.2 molar at pH 7 and the temperature is at least about 50° C. Other factors may significantly affect the stringency of hybridization, including, among others, base composition and size of the complementary strands, the presence of organic solvents such as formamide, and the extent of base mismatching. A preferred embodiment will include nucleic acids which will bind to disclosed sequences in 50% formamide and 200 nM NaCl at 42° C. See, e.g., Sambrook, et al.

An isolated BS10.55 or YTF03 protein DNA can be readily modified by nucleotide substitutions, nucleotide deletions, nucleotide insertions, and short inversions of nucleotide stretches. These modifications result in novel DNA sequences which encode BS10.55 or YTF03 protein antigens, their derivatives, or proteins having highly similar physiological, immunogenic, or antigenic activity.

Modified sequences can be used to produce mutant antigens or to enhance expression. Enhanced expression may involve gene amplification, increased transcription, increased translation, and other mechanisms. Such mutant BS10.55 or YTF03 protein derivatives include predetermined or site-specific mutations of the respective protein or its fragments. "Mutant BS10.55 or YTF03 protein" encompasses a polypeptide otherwise falling within the homology definition of the human BS10.55 or YTF03 protein as set forth above, but having an amino acid sequence which differs from that of a BS10.55 or YTF03 protein as found in nature, whether by way of deletion, substitution, or insertion. In particular, "site specific mutant BS10.55 or YTF03 protein" generally includes proteins having significant similarity with a protein having a sequence of SEQ ID NO: 2 or 4, and as sharing various biological activities, e.g., antigenic or immunogenic, with those sequences, and in preferred embodiments contain most or all of the disclosed sequence. This applies also to polymorphic variants from different individuals. Similar concepts apply to different BS10.55 or YTF03 proteins, particularly those found in various warm blooded animals, e.g., mammals and birds. As stated before, it is emphasized that descriptions are generally meant to encompass other BS10.55 or YTF03 proteins, not limited to the human embodiments specifically discussed.

Although site specific mutation sites are predetermined, mutants need not be site specific. BS10.55 or YTF03 protein mutagenesis can be conducted by making amino acid insertions or deletions. Substitutions, deletions, insertions, or combinations may be generated to arrive at a final construct. Insertions include amino- or carboxyl- terminal fusions, e.g. epitope tags. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also, Sambrook, et al. (1989) and Ausubel, et al. (1987 and Supplements). The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a BS10.55 or YTF03 protein polypeptide is a continuous protein molecule having sequences fused in a typical peptide linkage, typically made as a single translation product and exhibiting properties derived from each source peptide. A similar concept applies to heterologous nucleic acid sequences. Antibody fusion proteins are also contemplated.

In addition, new constructs may be made from combining similar functional domains from other proteins. For example, protein-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992. Thus, new chimeric polypeptides exhibiting new combinations of specificities will result from the functional linkage of protein-binding specificities and other functional domains.

VIII. Binding Agent:BS10.55 or Agent:YTF03 Protein Complexes

A BS10.55 or YTF03 protein that specifically binds to or that is specifically immunoreactive with an antibody generated against a defined immunogen, such as an immunogen consisting of the amino acid sequence of SEQ ID NO: 2 or 4, is typically determined in an immunoassay. The immunoassay uses a polyclonal antiserum which was raised to a protein of SEQ ID NO: 2 or 4. This antiserum is selected to have low crossreactivity against other proteases and any such crossreactivity is removed by immunoabsorption prior to use in the immunoassay.

In order to produce antisera for use in an immunoassay, the protein of SEQ ID NO: 2 or 4 is isolated as described herein. For example, recombinant protein may be produced in a mammalian cell line. An inbred strain of mice such as balb/c is immunized with the protein of SEQ ID NO: 2 or 4 using a standard adjuvant, such as Freund's adjuvant, and a standard mouse immunization protocol (see Harlow and Lane, supra). Alternatively, a synthetic peptide, preferably near full length, derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against other proteases or oxidoreductases, e.g., using a competitive binding immunoassay such as the one described in Harlow and Lane, supra, at pages 570–573. Preferably two related proteins are used in this determination in conjunction with either BS10.55 or YTF03 protein.

Immunoassays in the competitive binding format can be used for the crossreactivity determinations. For example, a protein of SEQ ID NO: 2 or 4 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 2 or 4. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorbtion with the above-listed proteins.

The immunoabsorbed and pooled antisera are then used in a competitive binding immunoassay as described above to compare a second protein to the immunogen protein (e.g., the protein motif of SEQ ID NO: 2 or 4). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein of SEQ ID NO: 2 or 4 that is required, then the second protein is said to specifically bind to an antibody generated to the immunogen.

It is understood that BS10.55 or YTF03. proteins are families of homologous proteins that comprise two or more genes. For a particular gene product, such as the human BS10.55 or YTF03 proteins, the term refers not only to the amino acid sequences disclosed herein, but also to other proteins that are polymorphic, allelic, non-allelic, or species variants or equivalents. It is also understood that the term "human BS10.55 or YTF03 protein" includes equivalent proteins, e.g., nonnatural mutations introduced by deliberate mutation using conventional recombinant technology such as single site mutation, or by excising short sections of DNA encoding BS10.55 or YTF03 proteins, or by substituting new amino acids, or adding new amino acids. Such minor alterations must substantially maintain the immunoidentity of the original molecule and/or its biological activity. Thus, these alterations include proteins that are specifically immunoreactive with a designated naturally occurring BS10.55 or YTF03 protein, for example, the human BS10.55 or YTF03 protein shown in SEQ ID NO: 2 or 4. The biological properties of the altered proteins can be determined by expressing the protein in an appropriate cell line and measuring, e.g., enzymatic activity uncer appropriate conditions. Particular protein modifications considered minor would include conservative substitution of amino acids with similar chemical properties, as described above for BS10.55 or YTF03 protein families as a whole. By aligning a protein optimally with the protein of SEQ ID NO: 2 or 4, and by using the conventional immunoassays described herein to determine immunoidentity, or by using lymphocyte chemotaxis assays, one can determine the protein compositions of the invention.

IX. Functional Variants

The blocking of physiological response to BS10.55 or YTF03 protein may result from the inhibition of enzymatic activity of the protein against its substrate, e.g., through competitive inhibition. Thus, in vitro assays of the present invention will often use isolated protein, membranes from cells expressing a recombinant membrane associated proteins, soluble fragments comprising enzymatically active segments of these proteins, or fragments attached to solid phase substrates. These assays will also allow for the diagnostic determination of the effects of either binding segment mutations and modifications, or protein mutations and modifications, e.g., protein analogs. This invention also contemplates the use of competitive drug screening assays, e.g., where neutralizing antibodies to antigen or enzyme fragments compete with a test compound for binding to the protein. In this manner, the antibodies can be used to detect the presence of a polypeptide which shares one or more antigenic binding sites of the protein and can also be used to occupy binding sites on the protein that might otherwise interact with, e.g., substrate.

"Derivatives" of BS10.55 or YTF03 proteins include amino acid sequence mutants, glycosylation variants, and covalent or aggregate conjugates with other chemical moieties. Covalent derivatives can be prepared by linkage of functionalities to groups which are found in BS10.55 or YTF03 protein amino acid side chains or at the N- or C-termini, e.g., by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are typically selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents.

A major group of derivatives are covalent conjugates of the BS10.55 or YTF03 protein or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Fusion polypeptides between human BS10.55 or YTF03 proteins and other homologous or heterologous proteins are also provided. Heterologous polypeptides may be fusions between different related proteins, resulting in, e.g., a hybrid protein exhibiting modified substrate or other binding specificity. Likewise, heterologous fusions may be constructed which would exhibit a combination of properties or activities of the derivative proteins. Typical examples are fusions of a reporter polypeptide, e.g., luciferase, with a segment or domain of a protein, e.g., a receptor-binding segment, so that the presence or location of the fused protein may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

This invention also contemplates the use of derivatives of BS10.55 or YTF03 proteins other than variations in amino acid sequence or glycosylation. Such derivatives may involve covalent or aggregative association with chemical moieties. These derivatives generally include the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a BS10.55 or YTF03 protein can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-BS10.55 or anti-YTF03 protein antibodies. The BS10.55 or YTF03 proteins can also be labeled with a detectable group, e.g., radioiodinated by the chloramine T procedure, covalently bound to rare earth chelates, or conjugated to another fluorescent moiety for use in diagnostic assays. Purification of BS10.55 or YTF03 proteins may be effected by immobilized antibodies or substrate.

Isolated BS10.55 or YTF03 protein genes will allow transformation of cells lacking expression of corresponding BS10.55 or YTF03 proteins, e.g., either species types or cells which lack corresponding proteins and exhibit negative background activity. Expression of transformed genes will allow isolation of antigenically pure cell lines, with defined or single specie variants. This approach will allow for more sensitive detection and discrimination of the physiological effects of BS10.55 or YTF03 protein substrate proteins. Subcellular fragments, e.g., cytoplasts or membrane fragments, can be isolated and used.

X. Uses

The present invention provides reagents which will find use in diagnostic applications as described elsewhere herein, e.g., in the general description for metabolic abnormalities, or below in the description of kits for diagnosis.

BS10.55 or YTF03 protein nucleotides, e.g., human BS10.55 or YTF03 protein DNA or RNA, may be used as a component in a forensic assay. For instance, the nucleotide sequences provided may be labeled using, e.g., $^{32}$P or biotin and used to probe standard restriction fragment polymorphism blots, providing a measurable character to aid in distinguishing between individuals. Such probes may be used in well-known forensic techniques such as genetic fingerprinting. In addition, nucleotide probes made from BS10.55 or YTF03 protein sequences may be used in in situ assays to detect chromosomal abnormalities.

Antibodies and other binding agents directed towards BS10.55 or YTF03 proteins or nucleic acids may be used to purify the corresponding BS10.55 or YTF03 protein molecule. As described in the Examples below, antibody purification of BS10.55 or YTF03 protein components is both possible and practicable. Antibodies and other binding agents may also be used in a diagnostic fashion to determine whether BS10.55 or YTF03 protein components are present in a tissue sample or cell population using well-known techniques described herein. The ability to attach a binding agent to a BS10.55 or YTF03 protein provides a means to diagnose disorders associated with BS10.55 or YTF03 protein misregulation. Antibodies and other BS10.55 or YTF03 protein binding agents may also be useful as histological or sorting markers. As described in the examples below, BS10.55 or YTF03 protein expression is limited to specific tissue types. By directing a probe, such as an antibody or nucleic acid to a BS10.55 or YTF03 protein, it is possible to use the probe to distinguish tissue and cell types in situ or in vitro.

This invention also provides reagents with significant therapeutic value. The BS10.55 or YTF 3protein (naturally occurring or recombinant), fragments thereof, and antibodies thereto, along with compounds identified as having binding affinity to a BS10.55 or YTF03 protein, are useful in the treatment of conditions associated with abnormal metabolism, physiology, or development, including abnormal immune responsiveness or non-responsiveness. Abnormal proliferation, regeneration, degeneration, and atrophy may be modulated by appropriate therapeutic treatment using the compositions provided herein. The BS10.55 or YTF03 proteins likely play roles in regulation or development of hematopoietic cells, e.g., lymphoid cells, which affect immunological responses. Thus, for example, an antagonist of a BS10.55 or YTF03 protein could be useful in blocking the conversion of an immature or inactive immunologically relevant pro-protein to the mature or active form. Since the BS10.55 proteases were derived from dendritic cells, antagonists could also be important in preventing antigen processing and/or subsequent presentation.

Other abnormal developmental conditions are known in cell types shown to possess BS10.55 or YTF03 protein encoding mRNA by northern blot analysis. See Berkow (ed.) *The Merck Manual of Diagnosis and Therapy*, Merck & Co., Rahway, N.J.; and Thorn, et al. *Harrison's Principles of*

*Internal Medicine*, McGraw-Hill, N.Y. Developmental or functional abnormalities, e.g., of the immune system, cause significant medical abnormalities and conditions which may be susceptible to prevention or treatment using compositions provided herein.

Recombinant BS10.55 or YTF03 protein antibodies can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or fragments thereof can identify compounds having binding affinity to BS10.55 or YTF03 protein, including isolation of associated components. Various substrate candidates can be screened. Subsequent biological assays can then be utilized to determine if the compound has intrinsic enzyme blocking activity. Likewise, a compound having intrinsic stimulating activity might activate the activity of a BS10.55 or YTF03 protein. This invention further contemplates the therapeutic use of antibodies to BS10.55 or YTF03 protein as antagonists. This approach should be particularly useful with other BS10.55 or YTF03 protein polymorphic or species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

BS10.55 or YTF03 proteins, fragments thereof; antibodies to it or its fragments; antagonists; and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa.; Avis, et al. (eds.) (1993) *Pharmaceutical Dosage Forms: Parenteral Medications* Dekker, N.Y.; Lieberman, et al. (eds.) (1990) *Pharmaceutical Dosage Forms: Tablets* Dekker, N.Y.; and Lieberman, et al. (eds.) (1990) *Pharmaceutical Dosage Forms: Disperse Systems* Dekker, N.Y. The therapy of this invention may be combined with or used in association with other therapeutic agents.

Both the naturally occurring and the recombinant forms of the BS10.55 or YTF03 proteins of this invention are particularly useful in kits and assay methods which are capable of screening compounds for binding activity to the proteins, including substrates or competitive inhibitors. Several methods of automating assays have been developed in recent years so as to permit screening of tens of thousands of compounds in a short period. See, e.g., Fodor, et al. (1991) *Science* 251:767–773, and other descriptions of chemical diversity libraries, which describe means for testing of binding affinity by a plurality of compounds. The development of suitable assays can be greatly facilitated by the availability of large amounts of purified, soluble BS10.55 or YTF03 protein as provided by this invention.

For example, antagonists can normally be found once the protein has been structurally defined. Testing of potential substrates or analogs is now possible upon the development of highly automated assay methods using a purified enzyme. In particular, new agonists and antagonists will be discovered by using screening techniques described herein. Of particular importance are compounds found to have a combined blockage activity for multiple BS10.55 or YTF03 protein substrates, e.g., compounds which can serve as antagonists for polymorphic or species variants of a BS10.55 or YTF03 protein.

This invention is particularly useful for screening compounds by using recombinant protein in a variety of drug screening techniques. The advantages of using a recombinant protein in screening for specific ligands include: (a) improved renewable source of the BS10.55 or YTF03 protein from a specific source; (b) potentially greater number of molecules per cell giving better signal to noise ratio in assays; and (c) species variant specificity (theoretically giving greater biological and, disease specificity).

One method of drug screening utilizes eukaryotic or prokaryotic host cells which are stably transformed with recombinant DNA molecules expressing a BS10.55 or YTF03 protein substrate. Cells may be isolated which express a substrate in isolation from any others. Such cells, either in viable or fixed form, can be used for standard enzyme/substrate cleavage or oxidoreductase assays. See also, Parce, et al. (1989) *Science* 246:243–247; and Owicki, et al. (1990) *Proc. Nat'Acad. Sci. USA* 87:4007–4011, which describe sensitive methods to detect cellular responses. Competitive assays are particularly useful, where the cells (source of BS10.55 or YTF03 protein) or homogenates are contacted and incubated with a labeled antibody having known binding affinity to the protein, such as $^{125}$I-antibody, and a test sample whose binding affinity to the binding composition is being measured. The bound and free labeled binding compositions are then separated to assess the degree of antigen binding. The amount of test compound bound is inversely proportional to the amount of labeled reagent binding to the known source. Any one of numerous techniques can be used to separate bound from free antigen to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on BS10.55 or YTF03 protein mediated functions, e.g., substrate cleavage, oxidoreductase activity, and others. Some detection methods allow for elimination of a separation step, e.g., a proximity sensitive detection system.

Another method utilizes solubilized, unpurified or solubilized, purified BS10.55 or YTF03 protein from tansformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to a BS10.55 or YTF03 protein, e.g., an antibody, is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al., supra. Then all the pins are reacted with solubilized, unpurified or solubilized, purified BS10.55 or YTF03 protein antibody, and washed. The next step involves detecting bound BS10.55 or YTF03 protein antibody.

Rational drug design may also be based upon structural studies of the molecular shapes of the BS10.55 or YTF03 protein and other effectors or analogs. See, e.g., *Methods in Enzymology* vols 202 and 203. Effectors may be other proteins which mediate other functions in response to antigen binding, or other proteins which normally interact with the substrate. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography* Academic Press, NY.

A purified BS10.55 or YTF03 protein can be coated directly onto plates for use in the aforementioned drug screening techniques. However, non-neutralizing antibodies to these antigens can be used as capture antibodies to immobilize the respective antigen on the solid phase.

XI. Kits

This invention also contemplates use of BS10.55 or YTF03 proteins, fragments thereof, peptides, and their fusion products in a variety of diagnostic kits and methods for detecting the presence of BS10.55 or YTF03 protein or a BS10.55 or YTF03 protein substrate. Typically the kit will have a compartment containing either a defined BS10.55 or YTF03 peptide or gene segment or a reagent which recognizes one or the other, e.g., substrates or antibodies.

A kit for determining the binding affinity of a test compound to a BS10.55 or YTF03 protein would typically comprise a test compound; a labeled compound, e.g., an antibody having known binding affinity for the BS10.55 or YTF03 protein; a source of BS10.55 or YTF03 protein (naturally occurring or recombinant); and a means for separating bound from free labeled compound, such as a solid phase for immobilizing the BS10.55 or YTF03 protein. Once compounds are screened, those having suitable binding affinity to the BS10.55 or YTF03 protein can be evaluated in suitable biological assays, as are well known in the art, to determine whether they act as agonists or antagonists to a substrate. The availability of recombinant BS10.55 or YTF03 polypeptides also provide well defined standards for calibrating such assays.

A preferred kit for determining the concentration of, for example, a BS10.55 or YTF03 protein in a sample would typically comprise a labeled compound, e.g., antibody, having known binding affinity for the BS10.55 or YTF03 protein, a source of BS10.55 or YTF03 protein (naturally occurring or recombinant), and a means for separating the bound from free labeled compound, for example, a solid phase for immobilizing the BS10.55 or YTF03 protein. Compartments containing reagents, and instructions, will normally be provided.

Antibodies, including antigen binding fragments, specific for the BS10.55 or YTF03 protein, or fragments thereof, are useful in diagnostic applications to detect the presence of elevated levels of BS10.55 or YTF03 protein and/or its fragments. Such diagnostic assays can employ lysates, live cells, fixed cells, immunofluorescence, cell cultures, body fluids, and further can involve the detection of antigens related to the ligand in serum, or the like. Diagnostic assays may be homogeneous (without a separation step between free reagent and BS10.55 or YTF03 protein complex) or heterogeneous (with a separation step). Various commercial assays exist, such as radioimmunoassay (RIA), enzyme-linked immunosorbentassay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a BS10.55 or YTF03 protein or to a particular fragment thereof. Similar assays have also been extensively discussed in the literature. See, e.g., Harlow and Lane (1988) *Antibodies: A Laboratory Manual,* CSH Press, NY; Chan (ed.) (1987) *Immunoassay: A Practical Guide* Academic Press, Orlando, Fla.; Price and Newman (eds. ) (1991) *Principles and Practice of Immunoassay* Stockton Press, NY; and Ngo (ed.) (1988) *Nonisotopic Immunoassay* Plenum Press, NY.

Anti-idiotypic antibodies may have similar use to diagnose presence of antibodies against a BS10.55 or YTF03 protein, as such may be diagnostic of various abnormal states. For example, overproduction of BS10.55 or YTF03 protein may result in production of various immunological or other medical reactions which may be diagnostic of abnormal physiological states, e.g., in cell growth, acitivation, or differentiation.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled BS10.55 or YTF03 protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification, or may be modified in a variety of ways. For example, labeling may be achieved by covalently or non-covlalently joining a moiety which directly or indirectly provides a detectable signal. In any of these assays, the protein, test compound, BS10.55 or YTF03 protein, or antibodies thereto can be labeled either directly or indirectly. Possibilities for direct labeling include label groups: radio-labels such as 125I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free antigen, or alternatively the bound from the free test compound. The BS10.55 or YTF03 protein can be immobilized on various matrices followed by washing. Suitable matrices include plastic such as an ELISA plate, filters, and beads. Methods of immobilizing the BS10.55 or YTF03 protein to a matrix include, without limitation, direct adhesion to plastic, use of a capture antibody, chemical coupling, and biotin-avidin. The last step in this approach usually involves the precipitation of enzyme/antibody or enzyme substrate complex by various methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves us e of oligonucleotide or polynucleotide sequences taken from the sequence of a BS10.55 or YTF03 protein. These sequences can be used as probes for detecting levels of the BS10.55 or YTF03 protein message in samples from natural sources, or patients suspected of having an abnormal condition, e.g., immune problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various detectable labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out using many conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

XII. Substrate Identification

Having isolated a protease or oxidoreductase, methods exist for identifying a target substrate. For example, a candidate substrate can be contacted with a BS10.55 or YTF03 protein in an enzymatic reaction. The resulting cleavage or oxidoreduction product can be analyzed, e.g., using SDS-PAGE, HPLC, spectroscopy or other forms of analysis. For example, the molecular weight of a protease cleavage product should be compared against the molecular weights of the uncleaved substrate and the BS10.55 protein. The successful candidate substrate will exhibit a shift to a lower molecular weight. Analysis of the substrate should determine what site specificity may exist for the enzyme under the tested conditions. Alternatively, if the protease acts by transforming an inactive substrate to the active form, the resulting activity can be assayed, e.g., by the result of the activated factor, e.g., proliferation, apoptosis, or activation of a target cell.

Sequence specificity of products may allow search through sequence databases to identify candidate proteins as physiologically natural substrates. Alternatively, the protease may be involve in antigen processing and presentation to appropriate immune cells.

Correspondingly, various candidate oxidation or reduction substrates may be evaluated. A spectroscopic or other method may indicate what the enzyme has specificity for acting on.

The broad scope of this invention is best understood with reference to the following examples, which are not intended to limit the invention to specific embodiments.

EXAMPLES

I. General Methods

Many of the standard methods below are described or referenced, e.g., in Maniatis, et al. (1982) *Molecular Cloning, A Laboratory Manual* Cold Spring Harbor Laboratory, Cold Spring Harbor Press, NY; Sambrook, et al. (1989) *Molecular Cloning: A Laboratory Manual* (2d ed.) Vols. 1–3, CSH Press, NY; Ausubel, et al., *Biology* Greene Publishing Associates, Brooklyn, N.Y.; or Ausubel, et al. (1987 and Supplements) *Current Protocols in Molecular Biology* Wiley/Greene, NY; Innis, et al. (eds.) (1990) *PCR Protocols: A Guide to Methods and Applications* Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments (epitope tags), e.g., to a FLAG sequence or an equivalent which can be fused, e.g., via a protein-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering. Principle and Methods* 12:87–98, Plenum Press, NY; and Crowe, et al. (1992) *QIAexpress: The High Level Expression & Protein Purification System* QUIAGEN, Inc., Chatsworth, Calif.

Standard immunological techniques are described, e.g., in Coligan (1991) *Current Protocols in Immunology* Wiley/Greene, NY; and *Methods in Enzymology* volumes. 70, 731 74, 84, 92, 93, 108, 116, 121, 132, 150, 162, and 163. Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melamed, et al. (1990) *Flow Cytometry and Sorting* Wiley-Liss, Inc., New York, N.Y.; Shapiro (1988) *Practical Flow Cytometry* Liss, New York, NY; and Robinson, et al. (1993) *Handbook of Flow Cytometry Methods* Wiley-Liss, New York, N.Y.

II. Isolation of Human BS10.55 or YTF03 Protein

A clone encoding the human BS10.55 or YTF03 protein is isolated from a natural source by many different possible methods. Given the sequences provided herein, PCR primers or hybridization probes are selected and/or constructed to isolate a nucleic acid, e.g., genomic DNA segments or cDNA reverse transcripts. Appropriate cell sources include human tissues, e.g., brain libraries. Tissue distribution below also suggests source tissues. Genetic and polymorphic or allelic variants are isolated by screening a population of individuals.

The BS10.55 gene was originally isolated from human germinal center dendritic cells (Grouard, et al. (1996) *Nature* 384:364–367) stimulated by overnight incubation with the anti-CD40 monoclonal antibody G28–5 (provided by E. A. Clark and J. F. Cantaloube). The PCR fragments were cloned via T-overhang into pCRII (Invitrogen).

cDNA was prepared from $3 \times 10^6$ germinal center dendritic cells purified from human tonsils to 99% homogeneity and CD40 activated. The cDNA was cut by the RsaI restriction enzyme and subtracted against cDNA from the cell line U937. U937 (ATCC CRL-1593) is a human is histiocytic lymphoma expressing many monocyte-like characteristics. The subtraction procedure described recently by Diatchenko, et al. (1996) *Proc. Natl. Acad. Sci USA* 93:6025–6030, was used with an adaptation to low cell number. The clone BS10.55 was discovered by random sequencing of the subtracted germinal center dendritic cell library. The cDNA was extended by RACE (rapid amplification of cohesive ends) using cDNA from in vitro generated dendritic cells. Caux, et al. (1992) *Nature* 360:258–261.

The YTF03 gene was found in a cDNA library made from a population of 90% CD1a+dendritic cells, proliferated in TNF-α and GM-CSF.

PCR based detection is performed by standard methods, preferably using appropriate primers from opposite ends of the coding sequence, but flanking segments might be selected for specific purposes.

Alternatively, hybridization probes are selected. Particular AT or GC contents of probes are selected depending upon the expected homology and mismatching expected. Appropriate stringency conditions are selected to balance an appropriate positive signal to background ratio. Successive washing steps are used to identify clones of greater homology.

Further clones will be isolated, e.g., using an antibody based selection procedure. Standard expression cloning methods are applied including, e.g., FACS staining of membrane associated expression product. The antibodies are used to identify clones producing a recognized protein. Alternatively, antibodies are used to purify a BS10.55 or YTF03 protein, with protein sequencing and standard means to isolate a gene encoding that protein.

Genomic or cDNA sequence based methods will also allow for identification of sequences naturally available, or otherwise, which exhibit homology to the provided sequences.

III. Isolation of Mouse BS10.55 or YTF03 Protein

Similar methods are used as above to isolate an appropriate BS10.55 or YTF03 protein gene. Similar source materials as indicated above are used to isolate natural genes, including genetic, polymorphic, allelic, or strain variants. Species variants are also isolated using similar methods. Various sequence databases may suggest related or counterpart sequences. See, e.g., Capone, et al. (1996) *J. Immunol.* 157:969–973.

IV. Isolation of an Avian BS10.55 or YTF03 Protein Clone

An appropriate avian source is selected as above. Similar methods are utilized to isolate other species variants, though the level of similarity will typically be lower for avian BS10.55 or YTF03 protein as compared to a human to mouse sequence.

V. Expression; Purification; Characterization

With an appropriate clone from above, the coding sequence is inserted into an appropriate expression vector. This may be in a vector specifically selected for a prokaryote, yeast, insect, or higher vertebrate, e.g., mammalian expression system. Standard methods are applied to produce the gene product, preferably as a soluble secreted molecule, but will, in certain instances, also be made as an intracellular protein. Intracellular proteins typically require cell lysis to recover the protein, and insoluble inclusion bodies are a common starting material for further purificiation.

With a clone encoding a vertebrate BS10.55 or YTF03 protein, recombinant production means are used, although natural forms may be purified from appropriate sources, e.g., expressing cell lines. The protein product is purified by standard methods of protein purification, in certain cases, e.g., coupled with immunoaffinity methods. Immunoaffinity methods are used either as a purification step, as described above, or as a detection assay to determine the partition properties of the protein.

Preferably, the protein is secreted into the medium, and the soluble product is purified from the medium in a soluble form. Standard purification techniques applied to soluble protiens are then applied, with enzyme assays or immunodetection methods useful for following where the protease purifies. Alternatively, as described above, inclusion bodies from prokaryotic expression systems are a useful source of material. Typically, the insoluble protein is solubilized from the inclusion bodies and refolded using standard methods. Purification methods are developed as described above.

In certain embodiments, the protein is made in a eukaryotic cell which glycosylates the protein normally. The purification methods may be affected thereby, as may biological activities. The intact protein can be processed to release the protein domain, probably due to a cleavage event. While recombinant protein appears to be processed, the physiological processes which normally do such in native cells remain to be determined.

The product of the purification method described above is characterized to determine many structural features. Standard physical methods are applied, e.g., amino acid analysis and protein sequencing. The resulting protein is subjected to CD spectroscopy and other spectroscopic methods, e.g., NMR, ESR, mass spectroscopy, etc. The product is characterized to determine its molecular form and size, e.g., using gel chromatography and similar techniques. Understanding of the chromatographic properties will lead to more gentle or efficient purification methods.

Prediction of glycosylation sites may be made, e.g., as reported in Hansen, et al. (1995) *Biochem. J.* 308:801–813. Standard methods for assaying oxidoreductases, particularly monoamine oxidases, are found, e.g., in Methods in Enzymology; Moser, et al. (1995) *J. Bioenerg.* 27 263–274; Lawen, et al. (1994) *Mol. Aspects Med.* 15:supp:13–27; and Koishi, et al. (1997) *J. Biol. Chem.* 272:2570–2577.

VI Preparation of Antibodies Against Vertebrate BS10.55 or YTF03 Protein

With protein produced and purified, as above, animals are immunized to produce antibodies. Polyclonal antiserum may be raised using non-purified antigen, though the resulting serum will exhibit higher background levels. Preferably, the antigen is purified using standard protein purification techniques, including, e.g., affinity chromatography using polyclonal serum indicated above. Presence of specific antibodies is detected using defined synthetic peptide fragments.

Alternatively, polyclonal serum is raised against a purified antigen, purified as indicated above, or using synthetic peptides. A series of overlapping synthetic peptides which encompass all of the full length sequence, if presented to an animal, will produce serum recognizing most linear epitopes on the protein. Such an antiserum is used to affinity purify protein. This purified protein, in turn, may be used to immunize another animal to produce another antiserum preparation.

Standard techniques are used to generate induce monoclonal antibodies to either unpurified antigen, or, preferably, purified antigen.

VII. Cellular and Tissue Distribution

Distribution of the protein or gene products are determined, e.g., using immunohistochemistry with an antibody reagent, as produced above, or by screening for nucleic acids encoding the BS10.55 or YTF03 protein. Either hybridization or PCR methods are used to detect DNA, cDNA, or message content. Histochemistry allows determination of the specific cell types within a tissue which express higher or lower levels of message or DNA. Antibody techniques are useful to quantitate protein in a biological sample, including a liquid or tissue sample. Immunoassays are developed to quantitate protein.

Hybridization techniques were applied to the tissue types in described above with positive or negative results, as indicated. The commercial tissue blots may have more significant cellular contamination from other cells, e.g., from blood or other cells which are in the tissue.

By PCR the BS10.55 sequence is expressed in germinal center dendritic cells and in vitro generated dendritic cells, either stimulated or non-stimulated (Caux, et al. (1992) *Nature* 360:258–261). A faint signal may have been detected in CHA kidney epithelial carcinoma cell line. No detectable signal was observed in the hematopoietic precursor line TF1, Jurkat T cell line, MRC5 lung fibroblast sarcoma cell line, JY B cell line, or U937 pre-monocytic cell line.

By Northern blot analyses a 2.9 kb message was detected in RNA from adult small intestine, but not in similar abundance in any of adult PBL, colon, ovary, testis, prostate, thymus, spleen, pancreas, kidney, skeletal muscle, liver, lung, placenta, brain, or heart. No signal was detected in resting DC, activated DC, monocytes, granulocytes, resting PBL, activated PBL, or B cells.

By PCR analysis, expression of YTF03 is strongest in monocyte M6 (elutriated monocytes activated with LPS 6 h), 70% DC (resting 70% CD1a+dendritic cells, proliferated in TNF-α and GM-CSF), D1 (dendritic cells stimulated 1 h in PMA and ionomycin), D6 (dendritic cells stimulated 6 h in PMA and ionomycin), HY06R (resting Th1 clone), and HY06α (activated with anti-peptide, anergic clone). Expression is almost as strong in Monocyte C+ (elutriated monocytes activated with LPS, IFN-γ, and IL-10), D5 DC (resting dendritic cells cultured 5 d in GM-CSF and IL-4), DC mix (dendritic cells stimulated with a mixture of cytokines), aid HY06A (activated with anti-CD28 and anti-CD3).

Expression of YTF03 is not as strong in C- (elutriated monocyte activated with LPS, IFN-γ, and anti-IL-10), M1 (elutriated monocytes activated with LPS 1 h), PBMCA (activated using T cell stimulation conditions, with anti-CD3 and PMA), HY935A (activated with anti-CD28 and anti-CD3), BC (pool of EBV transformed lines), SplenoA (splenocytes activated using B cell stimulating conditions, with anti-CD40 and IL-4), NKR (resting NK cell pool), NKA (NK cell pool activated 6 h with PMA and ionomycin; NKA is slightly stronger than NKR), and spleen. Signal is much weaker in U937 (pre-monocytic cell line), brain, small intestine, and very faint in HY935R (resting Th2 clone), adipose, and placenta. It is questionable whether YTF03 is expressed in kidney. No expression was detected in: PBMCR (resting PBMC), SplenoR (resting splenocytes), lung, liver, heart, gall bladder, ovary, testes, uterus, and RAW. In summary, YTF03 is expressed mainly in DC and monocytes, and to a lesser extent in some T cells.

VIII. Structure Activity Relationship

Information on the criticality of particular residues is determined using standard procedures and analysis. Standard mutagenesis analysis is performed, e.g., by generating many different variants at determined positions, e.g., at the positions identified above, and evaluating biological activities of the variants. This may be performed to the extent of determining positions which modify activity, or to focus on specific positions to determine the residues which can be substituted to either retain, block, or modulate biological activity.

Alternatively, analysis of natural variants can indicate what positions tolerate natural mutations. This may result from populational analysis of variation among individuals, or across strains or species. Samples from selected individuals are analysed, e.g., by PCR analysis and sequencing. This allows evaluation of population polymorphisms.

IX. Additional genes

One additional gene has been characterized and described. See Table 3. Nucleic acids may be used, as described above, to express and assay biological samples for hybridizing or related nucleic acids. They may also be used to express recombinant protein, which can be enriched or purified for the expression products. Those products can be used to further characterize biochemically and physiologically the protein. Antibodies may be made, both for diagnostic purposes, and to modulate biological activity of the protein itself. Such reagents may also have therapeutic applications, and can be used as described above. Protein and nucleic acid variants will be useful as described above.

TABLE 3

APD08 gene from a human, characteristic of primate embodiments.
The nucleotide and predicted amino acid sequence. SEQ ID NO: 5 and 6.
The coding sequence runs from about 69 to 1928.
The encoded protein contains two domains which each exhibit homology
to a GTPase. The amino terminal GTPase domain is similar to
the Rho family members, most of which are smaller proteins.
The cDNA appears to be widely expressed, but sequence should be
characteristic of genetic origin, and may be useful, e.g., in
differentiating genetic origin, or genetic relation. Thus, the
sequence may be useful in identifying human tissues. Related gene
sequences by comparison search using standard algorithms include,
e.g., those identified by GenBank numbers H07061, H13318, N52992,
H96929, H07062, R40014, and R13644.

```
GGGTCGACCA CGCGTCCGAC CAGGTCGGGG CCGGGTTCCG GGTCGGGGAG CGGCTCCGGG    60

CGGCAGCT ATG AGG CGG GAC GTG CGC ATC CTG TTA CTG GGC GAG GCC CAG    110
         Met Arg Arg Asp Val Arg Ile Leu Leu Leu Gly Glu Ala Gln
           1               5                  10
GTG GGG AAG ACG TCG CTG ATC CTG TCC CTG GTG GGC GAG GAG TTC CCC    158
Val Gly Lys Thr Ser Leu Ile Leu Ser Leu Val Gly Glu Glu Phe Pro
 15              20                  25                  30

GAG GAG GTC CCT CCC CGC GCG GAG GAG ATC ACG ATC CCC GCG GAC GTC    206
Glu Glu Val Pro Pro Arg Ala Glu Glu Ile Thr Ile Pro Ala Asp Val
                 35                  40                  45

ACC CCG GAG AAG GTG CCC ACC CAC ATC GTG GAC TAC TCA GAA GCC GAG    254
Thr Pro Glu Lys Val Pro Thr His Ile Val Asp Tyr Ser Glu Ala Glu
             50                  55                  60

CAG ACG GAC GAG GAG CTG CGG GAG GAG ATC CAC AAG GCA AAC GTG GTG    302
Gln Thr Asp Glu Glu Leu Arg Glu Glu Ile His Lys Ala Asn Val Val
         65                  70                  75

TGT GTG GTG TAT GAC GTC TCT GAG GAG GCC ACC ATT GAG AAG ATT CGA    350
Cys Val Val Tyr Asp Val Ser Glu Glu Ala Thr Ile Glu Lys Ile Arg
     80                  85                  90

ACT AAG TGG ATC CCA CTG GTG AAT GGG GGG ACC ACG CAG GGG CCC AGG    398
Thr Lys Trp Ile Pro Leu Val Asn Gly Gly Thr Thr Gln Gly Pro Arg
 95                 100                 105                 110

GTG CCC ATC ATC CTA GTG GGC AAC AAG TCA GAC CTG CGG TCG GGG AGC    446
Val Pro Ile Ile Leu Val Gly Asn Lys Ser Asp Leu Arg Ser Gly Ser
                115                 120                 125

TCC ATG GAG GCC GTG CTC CCC ATC ATG AGC CAG TTT CCC GAG ATT GAG    494
Ser Met Glu Ala Val Leu Pro Ile Met Ser Gln Phe Pro Glu Ile Glu
            130                 135                 140

ACC TGC GTG GAG TGT TCG GCC AAG AAC CTG AGG AAC ATC TCA GAG CTG    542
Thr Cys Val Glu Cys Ser Ala Lys Asn Leu Arg Asn Ile Ser Glu Leu
        145                 150                 155

TTC TAC TAC GCC CAG AAG GCC GTC CTG CAT CCC ACA GCC CCC CTC TAT    590
Phe Tyr Tyr Ala Gln Lys Ala Val Leu His Pro Thr Ala Pro Leu Tyr
    160                 165                 170

GAC CCT GAG GCC AAG CAG TTG AGG CCC GCG TGC GCC CAG GCG CTG ACG    638
Asp Pro Glu Ala Lys Gln Leu Arg Pro Ala Cys Ala Gln Ala Leu Thr
175                 180                 185                 190

CGC ATC TTC AGG CTC TCA GAT CAG GAC CTG GAC CAG GCG CTC AGT GAC    686
Arg Ile Phe Arg Leu Ser Asp Gln Asp Leu Asp Gln Ala Leu Ser Asp
                195                 200                 205

GAA GAG CTC AAC GCT TTC CAG CAG AAA TCC TGC TTT GGG CAC CCC CTG    734
Glu Glu Leu Asn Ala Phe Gln Gln Lys Ser Cys Phe Gly His Pro Leu
            210                 215                 220

GCC CCG CAG GCC CTG GAG GAC GTG AAG ACG GTG GTG TGC AGG AAC GTG    782
Ala Pro Gln Ala Leu Glu Asp Val Lys Thr Val Val Cys Arg Asn Val
        225                 230                 235

GCG GGC GGC GTG CGG GAG GAC CGG CTG ACC CTG GAT GGT TTC CTC TTC    830
Ala Gly Gly Val Arg Glu Asp Arg Leu Thr Leu Asp Gly Phe Leu Phe
    240                 245                 250
```

TABLE 3-continued

APD08 gene from a human, characteristic of primate embodiments.
The nucleotide and predicted amino acid sequence. SEQ ID NO: 5 and 6.
The coding sequence runs from about 69 to 1928.
The encoded protein contains two domains which each exhibit homology
to a GTPase. The amino terminal GTPase domain is similar to
the Rho family members, most of which are smaller proteins.
The cDNA appears to be widely expressed, but sequence should be
characteristic of genetic origin, and may be useful, e.g., in
differentiating genetic origin, or genetic relation. Thus, the
sequence may be useful in identifying human tissues. Related gene
sequences by comparison search using standard algorithms include,
e.g., those identified by GenBank numbers H07061, H13318, N52992,
H96929, H07062, R40014, and R13644.

```
CTG AAC ACG CTC TTC ATC CAG CGC GGC CGG CAC GAG ACC ACC TGG ACC      878
Leu Asn Thr Leu Phe Ile Gln Arg Gly Arg His Glu Thr Thr Trp Thr
255             260                 265                 270

ATC CTG CGG CGC TTC GGC TAC AGC GAT GCC CTG GAG CTG ACT GCG GAC      926
Ile Leu Arg Arg Phe Gly Tyr Ser Asp Ala Leu Glu Leu Thr Ala Asp
                275                 280                 285

TAT CTC TCC CCT CTG ATC CAC GTG CCC CCC GGC TGC AGC ACG GAG CTC      974
Tyr Leu Ser Pro Leu Ile His Val Pro Pro Gly Cys Ser Thr Glu Leu
            290                 295                 300

AAC CAC CTT GGC TAC CAG TTT GTG CAG AGA GTG TTT GAG AAG CAC GAC     1022
Asn His Leu Gly Tyr Gln Phe Val Gln Arg Val Phe Glu Lys His Asp
        305                 310                 315

CAG GAC CGC GAC GGC GCC CTC TCG CCC GTG GAG CTG CAA AGC CTT TTC     1070
Gln Asp Arg Asp Gly Ala Leu Ser Pro Val Glu Leu Gln Ser Leu Phe
    320                 325                 330

AGT GTG TTC CCA GCA GCG CCC TGG GGC CCC GAG CTC CCA CGC ACA GTC     1118
Ser Val Phe Pro Ala Ala Pro Trp Gly Pro Glu Leu Pro Arg Thr Val
335                 340                 345                 350

CGC ACA GAG GCC GGC CGG TTG CCC CTG CAC GGA TAC CTC TGC CAG TGG     1166
Arg Thr Glu Ala Gly Arg Leu Pro Leu His Gly Tyr Leu Cys Gln Trp
                355                 360                 365

ACC CTG GTG ACC TAC CTG GAC GTC CGG AGC TGC CTT GGA CAC CTA GGC     1214
Thr Leu Val Thr Tyr Leu Asp Val Arg Ser Cys Leu Gly His Leu Gly
            370                 375                 380

TAC CTG GGC TAC CCC ACC CTC TGT GAG CAG GAC CAG GCC CAT GCC ATC     1262
Tyr Leu Gly Tyr Pro Thr Leu Cys Glu Gln Asp Gln Ala His Ala Ile
        385                 390                 395

ACA GTC ACT CGT GAG AAG AGG CTG GAC CAG GAG AAG GGA CAG ACG CAG     1310
Thr Val Thr Arg Glu Lys Arg Leu Asp Gln Glu Lys Gly Gln Thr Gln
    400                 405                 410

TGG AGC GTC CTC CTG TGC AAG GTG GTA GGG GCC CGT GGA GTG GGC AAG     1358
Trp Ser Val Leu Leu Cys Lys Val Val Gly Ala Arg Gly Val Gly Lys
415                 420                 425                 430

TCT GCC TTC CTG CAG GCC TTT CTC GGC CGC GGC CTG GGG CAC CAG GAC     1406
Ser Ala Phe Leu Gln Ala Phe Leu Gly Arg Gly Leu Gly His Gln Asp
                435                 440                 445

ACG AGG GAG CAG CCT CCC GGC TAC GCC ATC GAC ACG GTG CAG GTC AAT     1454
Thr Arg Glu Gln Pro Pro Gly Tyr Ala Ile Asp Thr Val Gln Val Asn
            450                 455                 460

GGA CAG GAG AAG TAC TTG ATC CTC TGT GAG GTG GGC ACA GAT GGT CTG     1502
Gly Gln Glu Lys Tyr Leu Ile Leu Cys Glu Val Gly Thr Asp Gly Leu
        465                 470                 475

CTG GCC ACA TCG CTG GAC GCC ACC TGT GAC GTT GCC TGC TTG ATG TTT     1550
Leu Ala Thr Ser Leu Asp Ala Thr Cys Asp Val Ala Cys Leu Met Phe
    480                 485                 490

GAT GGC AGT GAC CCA AAG TCC TTT GCA CAT TGT GCC AGC GTC TAC AAG     1598
Asp Gly Ser Asp Pro Lys Ser Phe Ala His Cys Ala Ser Val Tyr Lys
495                 500                 505                 510
```

TABLE 3-continued

APD08 gene from a human, characteristic of primate embodiments.
The nucleotide and predicted amino acid sequence. SEQ ID NO: 5 and 6.
The coding sequence runs from about 69 to 1928.
The encoded protein contains two domains which each exhibit homology
to a GTPase. The amino terminal GTPase domain is similar to
the Rho family members, most of which are smaller proteins.
The cDNA appears to be widely expressed, but sequence should be
characteristic of genetic origin, and may be useful, e.g., in
differentiating genetic origin, or genetic relation. Thus, the
sequence may be useful in identifying human tissues. Related gene
sequences by comparison search using standard algorithms include,
e.g., those identified by GenBank numbers H07061, H13318, N52992,
H96929, H07062, R40014, and R13644.

```
CAC CAT TAC ATG GAC GGG CAG ACC CCC TGC CTC TTT GTC TCC TCC AAG      1646
His His Tyr Met Asp Gly Gln Thr Pro Cys Leu Phe Val Ser Ser Lys
                515                 520                 525

GCC GAC CTG CCC GAA GGT GTC GCG GTG TCT GGC CCA TCA CCG GCC GAG      1694
Ala Asp Leu Pro Glu Gly Val Ala Val Ser Gly Pro Ser Pro Ala Glu
                530                 535                 540

TTT TGC CGC AAG CAC CGG CTA CCC GCT CCC GTG CCG TTC TCC TGT GCT      1742
Phe Cys Arg Lys His Arg Leu Pro Ala Pro Val Pro Phe Ser Cys Ala
                545                 550                 555

GGC CCA GCC GAG CCC AGC ACC ACC ATC TTC ACC CAG CTC GCC ACC ATG      1790
Gly Pro Ala Glu Pro Ser Thr Thr Ile Phe Thr Gln Leu Ala Thr Met
            560                 565                 570

GCC GCC TTC CCA CAT TTG GTC CAC GCA GAG CTG CAT CCC TCT TCC TTC      1838
Ala Ala Phe Pro His Leu Val His Ala Glu Leu His Pro Ser Ser Phe
575                 580                 585                 590

TGG CTC CGG GGG CTG CTG GGG GTT GTC GGG GCC GCC GTG GCC GCA GTC      1886
Trp Leu Arg Gly Leu Leu Gly Val Val Gly Ala Ala Val Ala Ala Val
                595                 600                 605

CTC AGC TTC TCA CTC TAC AGG GTC CTG GTG AAG AGC CAG TGA              1928
Leu Ser Phe Ser Leu Tyr Arg Val Leu Val Lys Ser Gin *
                610                 615                 620

GGCCCCTGGT ACCCAAGCCC CCTCCCCTGA CCTGGGTGTG CCTCGCTGCT GGGGCTCTGC    1988

ACTTTTTGTT TCTGAAGGCA GTCGATCTGC AGCGGGGCCT TATGCTGCCA TGCACTGCCC    2108

TGGCTCCTGC CGGACCCCCA GCGTGGGCCG TGGCAGGTGG CTGAGCAGGA GCTCCCAAGT    2168

GCCGGCCACC GCTGTCAGGG ATTGCCCACC CCTGGGCATC ATGTGTGTGG GGCCGGGGAG    2228

CACAGGTGTG GGAGCTGGTG ACCCCAGACC CAGAATTCTC AGGGCTCTAC CCCCCTTTCC    2288

TGGTCCTAGG TGGCCAGTGG GTATGAGGAG GGCTGGAAGG CAGAGCTTTG GGCCAAAAGC    2348

AGGCGTTGGG GGGTCCCCCC TCAAGTTTGG AGCCGTTTCC GTGGTTGTAG CAGAGGACCG    2408

GAGGTTGGGT TCCTGATTAA ACTTCACTGT GTGTTTTCTA TCTCGGATCC CAGTCTCTGA    2468

AGACAACTTG CTTTGATTCA ACCTAAAAAA AAAAAAAAA  AAAAAAAA                 2516
```

The present invention provides a binding compound comprising an antibody binding site which specifically binds to primate APD08 protein; a nucleic acid comprising sequence encoding at least 12.amino acids of primate APD08 protein; a substantially pure protein which is specifically recognized by the above antibody binding site; a substantially pure primate APD08 protein or peptide thereof; and a fusion protein comprising a 30 amino acid sequence portion of primate APD08 protein sequence.

In certain binding compound embodiments, the antibody binding site is specifically immunoreactive with a protein of SEQ ID NO: 6; is raised against a purified or recombinantly produced primate APD08 protein; is immunoselected on a substantially purified or recombinantly produced primate APD08 protein; is in a monoclonal antibody, Fab, or F(ab)2; is detectably labeled; is attached to a solid substrate; is from a rabbit or mouse; binds with a Kd of at least about 300 mM; is fused to another protein segment: is in a chimeric antibody; or is coupled to another chemical moiety.

The invention also provides a method of making an antigen-antibody complex, comprising a step of contacting a primate biological sample to a specific binding antibody described. In preferred embodiments, the method further includes steps to purify the antigen or antibody.

Alternative embodiments provide an antibody binding site wherein the binding site is detected in a biological sample by a method comprising the steps of contacting a binding agent having an affinity for APD08 protein with the biological sample; incubating the binding agent with the biological sample to form a binding agent:APD08 protein complex; and detecting the complex. In certain embodiments, the biological sample is human, and the binding agent is an antibody.

The invention also provides kits containing a composition described above and instructional material for the use of the composition; or segregation of the composition into a container. Typically, the kit is used to make a qualitative or quantitative analysis.

The invention also embraces a cell comprising an antibody described above; a cell transfected with a nucleic acid described above or a cell comprising a fusion protein described above.

In nucleic acid embodiments, the nucleic acid may encode a polypeptide which specifically binds an antibody generated against an immunogen selected from the group consisting of the mature polypeptide of SEQ ID NO: 6. Alternatively, the nucleic acid may encode at least 12 amino acids of SEQ ID NO: 6; comprise sequence of at least about 39 nucleotides selected from protein coding portions of SEQ ID NO: 5; hybridize to SEQ ID NO: 5 under stringent wash conditions of at least 45° C. and less than about 150 mM salt; comprise sequence made by a synthetic method; be an expression vector; be detectably labeled; be attached to a solid substrate; be from human; bind with a Kd of at least about 300 $\mu$M; be fused to another nucleic acid segment; be coupled to another chemical moiety; be operably associated with promoter, ribosome binding site, or poly-A addition site; be a PCR product; be transformed into a cell, including a bacterial cell; be in a sterile composition; be capable of selectively hybridizing to a nucleic acid encoding an APD08 protein; comprise a natural sequence; comprise a mature protein coding segment of SEQ ID NO: 5; encode a GTPase active portion of APD08; be detected in a biological sample by a method comprising: contacting a biological sample with a nucleic acid probe capable of selectively hybridizing to said nucleic acid, incubating the nucleic acid probe with the biological sample to form a hybrid of the nucleic acid probe with complementary nucleic acid sequences present in the biological sample; and determining the extent of hybridization of the nucleic acid probe to the complementary nucleic acid sequences, including the method where the nucleic acid probe is capable of hybridizing to a nucleic acid encoding a mature polypeptide of SEQ ID NO 6.

In protein or polypeptide embodiments, the protein may bind with a Kd of at least about 300 $\mu$M to an antibody generated against an immunogen of the polypeptides of SEQ ID NO: 6; be immunoselected on an antibody which selectively binds a polypeptide of SEQ ID NO: 6; comprise sequence of at least 12 contiguous residues of SEQ ID NO: 6; exhibit a post-translational modification pattern distinct from natural APD08; be 3-fold or fewer substituted from natural sequence; be recombinantly produced; be denatured; have sequence of full length natural polypeptide; be detectably labeled; be attached to a solid substrate; be from human; be in a sterile composition; be fused to another protein segment; be coupled to another chemical moiety; comprise at least a fragment of at least 32 amino acid residues from a human APD08 protein; comprise mature polypeptide sequence of SEQ ID NO 6; be a soluble protein; be a naturally occurring protein; or be a GTPase active portion of APD08.

The invention also provides an isolated protein which specifically binds to an antibody generated against an immunogen which is the full length polypeptide of SEQ ID NO: 6. Preferably such protein binds to the antibody with a Kd of at least about 300 $\mu$M; is immunoselected on an antibody which selectively binds a polypeptide of SEQ ID NO: 6; comprises sequence of at least 12 contiguous residues of SEQ ID NO: 6; exhibits a post-translational modification pattern distinct from natural APD08; is 3-fold or fewer substituted from natural sequence; is recombinantly produced; is denatured; has sequence of full length natural polypeptide; is detectably labeled; is attached to a solid substrate; is from human; is in a sterile composition; is fused to another protein segment; is coupled to another chemical moiety; comprises at least a fragment of at least 32 amino acid residues from a human APD08 protein; comprises mature polypeptide sequence selected from SEQ ID NO 6; is a soluble protein; or comprises a GTPase activity of APD08.

In certain other embodiments, the invention embraces a fusion protein described above, which comprises sequence from an enzymatically active portion of SEQ ID NO: 6. Preferably such protein binds with a Kd of at least about 300 $\mu$M to an antibody generated against an immunogen having sequence of a polypeptide of SEQ ID NO. 6; is immunoselected on an antibody which selectively binds a polypeptide of SEQ ID NO: 6; comprises sequence of at least 12 contiguous residues of SEQ ID NO: 6; is recombinantly produced; is denatured; has sequence of full length natural polypeptide; is detectably labeled; is attached to a solid substrate; comprises sequence from human; is in a sterile composition; is fused to another protein segment; is coupled to another chemical moiety; comprises at least a fragment of at least 32 amino acid residues from a human APD08 protein; comprises mature polypeptide sequence from SEQ ID NO: 6; is a soluble protein; or comprises a GTPase activity of APD08.

The invention also provides a substantially pure protein described above which comprises a GTPase activity of APD08.

APD08 is tested for GTPase activity by methods well known in the art. Assays are described or referred to in, e.g., Dickey, et al. (eds. 1993) *GTPases in Biology*, vol. 108, parts I and II, Springer-Verlag, New York, N.Y.; Balch, et al. (eds. 1995) *Meth. Enzymol.* Vols. 255–257, Academic Press, San Diego, Calif.; Tapon, et al. (1997) *Curr. Opin. Cell Biol.* 9:86–92; Hotchin, et al. (1996) *Cancer Surv.* 27:311–322; Symons (1996) *Trends Biochem Sci.* 21:178–181; Hilgenfeld (1995) *Curr Opin. Struct. Biol.* 5:810–817; Nuoffer, et al. (1994) *Annu. Rev. Biochem.* 63:949–990; Spaargaren, et al. (1995) *Gene Expr.* 4:345–356; and Hall (1992) *Mol. Cell. Biol.* 3:475–479. Based upon this activity, the enzyme will be useful in screening for agonists and antagonists, and in modulating related biochemistry or metabolism. Similar methods to those described above will be used to identify the cells and tissue specificity of expression.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An isolated binding compound comprising the antigen-binding site of an antibody that specifically binds to a polypeptide comprising the amino acid sequence of SEQ ID No:4.

2. The binding compound of claim 1, wherein said binding compound:
    a) is a polyclonal antibody;
    b) is a monoclonal antibody;
    c) is a humanized antibody;
    d) is an Fab, F(ab)$_2$, or Fv fragment;
    e) is detectably labeled; or
    f) binds to the polypeptide comprising the amino acid sequence SEQ ID NO:4 with a Kd of at least about 300 μM.

3. The binding compound of claim 1, wherein said binding compound is detected in a biological sample by a method comprising the steps of:
    a) contacting said binding compound with said biological sample;
    b) incubating said binding compound with said biological sample to form a complex of the binding compound and the polypeptide comprising the amino acid sequence of SEQ ID NO:4; and
    c) detecting said complex.

4. A kit comprising the binding compound of claim 1, further comprising a compartment and in instructional material.

5. The kit of claim 4, wherein said kit is used for a qualitative or quantitative analysis of a polypeptide comprising the amino acid sequence of SEQ ID NO:4, or an antigenic fragment thereof.

6. An isolated animal cell comprising the binding compound of claim 1.

* * * * *

UNITED STATES PATENT AND TRADEMARK OFFICE
CERTIFICATE OF CORRECTION

PATENT NO. : 6,518,405 B1
DATED : February 11, 2003
INVENTOR(S) : Lynette M. Dowling, Constance F. Huffine and Daniel M. Gorman It is certified that error appears in the above-identified patent and that said Letters Patent is hereby corrected as shown below:

Column 2,
Line 14, please delete "YTF3" and replace it with -- YTF03 --.

Column 76,
Line 22, please delete "in".

Signed and Sealed this

Eighth Day of April, 2003

JAMES E. ROGAN
*Director of the United States Patent and Trademark Office*